US009403881B2

(12) United States Patent
Abad et al.

(10) Patent No.: US 9,403,881 B2
(45) Date of Patent: Aug. 2, 2016

(54) INSECTICIDAL PROTEINS AND METHODS OF USE

(71) Applicant: Pioneer Hi-Bred International, Johnston, IA (US)

(72) Inventors: Andre R Abad, Johnston, IA (US); Zhenglin Hou, Ankeny, IA (US); Lu Liu, Palo Alto, CA (US); Brad Poland, Monroe, IA (US); Ute Schellenberger, Palo Alto, CA (US); Ingrid Udranszky, Mountain View, CA (US); Jimei Wang, Johnston, IA (US); Jun-Zhi Wei, Palo Alto, CA (US); Thomas C. Wolfe, Des Moines, IA (US); Lan Zhou, Ankeny, IA (US); Genhai Zhu, San Jose, CA (US); Weiping Xie, East Palo Alto, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 457 days.

(21) Appl. No.: 13/803,634

(22) Filed: Mar. 14, 2013

(65) Prior Publication Data

US 2014/0283208 A1 Sep. 18, 2014

(51) Int. Cl.
| | |
|---|---|
| *C12N 15/82* | (2006.01) |
| *A01N 37/46* | (2006.01) |
| *A01N 37/18* | (2006.01) |
| *C07K 14/325* | (2006.01) |
| *A01N 63/02* | (2006.01) |

(52) U.S. Cl.
CPC .............. *C07K 14/325* (2013.01); *A01N 37/18* (2013.01); *A01N 37/46* (2013.01); *A01N 63/02* (2013.01); *C12N 15/8286* (2013.01)

(58) Field of Classification Search
None
See application file for complete search history.

(56) References Cited

U.S. PATENT DOCUMENTS

2009/0070896 A1 3/2009 Horita et al.
2012/0148497 A1 6/2012 Alves

OTHER PUBLICATIONS

Friedberg (Automated protein function prediction—the genomic challenge. Brief. Bioinformatics. 7:225-242, 2006).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*

Ito, et al, "Molecular Basis of Cell and Developmental Biology: A Bacillus thuringiensis Crystal Protein with Selective Cytocidal Action to Human Cells" The Journal of Biological Chemistry, (2004) 279:21282-21286.

GenBank: Accession AB099515.1 (2006).

Akiba, et al, Crystal Structure of the Parasporin-2 Bacillus thuringiensis Toxin That Recognizes Cancer Cells, Journal Molecular Biology, (2009) 386:121-133.

International Search Report and Written Opinion for International Application No. PCT/US2014/025286 completed Mar. 13, 2014.

* cited by examiner

*Primary Examiner* — Medina A Ibrahim

*Assistant Examiner* — Wayne Zhong

(74) *Attorney, Agent, or Firm* — Pioneer Hi-Bred Int'l

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are isolated insecticidal proteins and nucleic acids. The sequences find use in the construction of expression vectors for subsequent transformation into organisms of interest, as probes for the isolation of other homologous (or partially homologous) genes. The insecticidal proteins find use in controlling or killing lepidopteran, coleopteran, dipteran, fungal, hemipteran, and nematode pest populations and for producing compositions with insecticidal activity.

11 Claims, 6 Drawing Sheets

Figure 1

Alignment of MP467 with hydralysin from *Hydra vulgaris*

```
gi|74996299|sp|Q52SK7|HLYS_HYDAT |BACK| RecName: Full=Hydralysin
 gi|62632956|gb|AAX89442.1| hydralysin [Hydra vulgaris]
          Length = 244

Score =  277 bits (708), Expect = 4e-72
 Identities = 132/242 (54%), Positives = 173/242 (71%)

Query: 4    QEKLSFTDLPALKSSPESVRQAFTNKFGTKPDGISVNSETYFNAVKPAITEQYGHPCYKR 63
            +E L+F+DL   L SSP+SVR+AFTN +G  PDGISVN+ETYFNAVKPAITEQYGH CYKR
Sbjct: 3    KELLTFSDLSWLDSSPDSVRKAFTNSYGRTPDGISVNNETYFNAVKPAITEQYGHYCYKR 62

Query: 64   LGDFNYMKGDGKPPTSAIVGSNVAVNYGDEEATMTLEVQGSWQSEQSWSSESTTGLTISS 123
             G   +       PT A++GS++A N GD    T+T+ V G+W    SWS+  + G+T+ S
Sbjct: 63   TGQTKIVSQQLSDPTDAVLGSSIARNRGDSPVTLTVSVAGTWNDSTSWSTSAEAGVTMKS 122

Query: 124  KFTIEGFFESGMEFSVSTTVGETKTESESRTATASVQVTVPPRSKKQVTMVGTLKKESMN 183
            +F + GFF++G EFSVS T G++ + S   +++T+ +QVTVPPRSK  V MVG +KKE +
Sbjct: 123  EFEVSGFFKTGAEFSVSVTAGKSGSSSVEKSSTSQIQVTVPPRSKVTVNMVGIMKKEKVC 182

Query: 184  FRAPISVDGMFGANFPKRVQDHYFWFLGAGSVLTQTTGEITGTIKNTAVFDVHTEIGKTE 243
            F   PI+VDG FGANF   VQ HYFWF+     L++T+G I GTI + +VFDV TEIG +E
Sbjct: 183  FEVPITVDGSFGANFGSSVQGHYFWFMSTDQALSKTSGIIKGTIDHASVFDVSTEIGPSE 242

Query: 244  PL 245
            PL
Sbjct: 243  PL 244
```

Figure 2

Alignment of MP467 with Cry46Ab/Parasporin-2 from *Bacillus thuringiensis*

```
gi|51090285|dbj|BAD35170.1| |BACK| crystal protein [Bacillus
           thuringiensis] cry46Ab
           Length = 304

Score =  220 bits (561), Expect = 3e-57
 Identities = 113/253 (44%), Positives = 160/253 (63%), Gaps = 2/253 (0%)

Query: 3    IQEKLSFTDLPALKSSPESVRQAFTNKFGTKPDGISVNSETYFNAVKPAITEQYGHPCYK  62
            IQE L+F DLPAL SSP+SVR  F++ +GT PDGI++N+ETYF+AV+P IT QYGH CYK
Sbjct: 30   IQEYLTFNDLPALGSSPQSVRSRFSSIYGTNPDGIALNNETYFSAVQPPITVQYGHYCYK  89

Query: 63   RLGDFNYMKGDGKPPTSAIVGSNVAVNYGDEEATMTLEVQGSWQSEQSWSSESTTGLTIS  122
            +G   Y+      + I+  +   N +E  T T+ + GSW    + +S +TTGL I+
Sbjct: 90   NVGTVQYVNRPTDINPNVILAQDTLTNNTNEPFTTTITLTGSWTKSSTVTSSTTTGLKIT  149

Query: 123  SKFTIEGFFESGMEFSVSTTVGETKTESESRTATASVQVTVPPRSKKQVTMVGTLKKESM  182
            +K +I+  FE G E S STT+G ++   SE+ T + +V VTVP +S++ + +    +ES
Sbjct: 150  TKLSIKKVFEIGGEVSFSTTIGSSEATSETFTVSKAVTVTVPAQSRRNIQLTAKIARESA  209

Query: 183  NFRAPISVDGMFGANFPKRV---QDHYFWFLGAGSVLTQTTGEITGTIKNTAVFDVHTEIG  240
            +F API+VDG FGANFP+RV    HYFWF  A   VL  T+G +  GT+ N + FD   T +
Sbjct: 210  DFSAPITVDGYFGANFPRRVGPGGHYFWFNPARDVLNATSGTLRGTVTNVSSFDFQTVVQ  269

Query: 241  KTEPLTAEELSKL  253
                 L  AE+     L
Sbjct: 270  PAYSLLAEQQEAL  282
```

Figure 3

Sequence alignment of beta hairpin structures with alternating residues from MP467 and homologs

Sequence alignment of β hairpins with alternating residues

```
             *  *  *  *  *  *      *  *  *  *  *  *
467   120    PTGLTISSKFTISG---FFESQMFSVSTTVG
Ps2   117    TTGFKFTSKLSIKK---VFSIGEVSFSTTIG
Hdr   115    ETGVKMSSEFGVEG---AFRMSGEFSLTVSVG
ApT   203    KIGVFTSFKVSLRA---IARSKVFTSFEFNAS
Aer   238    KVTTKNFFKWFLVG---RTELSIEIAANQSKA
Epn   124    SIQATAKFTVFFNE---TGVSLTTSYSFANTNT
LSL   211    AVSTRFKAGVPIFS-STRFKVQISVINLWRWG
CPE    30    KVSINVNFSVGFTSFFIQASVSYGFSITIGRQ
Aph   115    TLIYGFNGNVTGDFT-GKIDGLIGANVGIGST
```

467  Mp67s
Ps2  Parasporin-2 from *Bacillus thuringiensis* (pdb: 2ztb)
Hdr  Hydralysin from Cnidaria
ApT  Alpha-toxin from *Clostridium septicum*
Aer  Aerolysin from Aeromonas (pdb: 1pre)
Epn  ε-toxin form *Clostridium perfringens* (pdb: 1uyj)
LSL  Hemolytic lectin from *Laetiporus sulphureus* (pdb: 1w3a)
CPE  Enterotoxin from *Clostridium perfringens* (pdb: 3am2)
Aph  Alpha-hemolysin from *Staphylococcus Aureus* (pdb: 7ahl)

Pore stem of α-hemolysin (pdb:7ahl)

The overall 3 Domain structure of MP467 and Cry 46A

Structural comparisons between MP467 homologs

Detail of Domain 1 of MP467

US 9,403,881 B2

INSECTICIDAL PROTEINS AND METHODS OF USE

REFERENCE TO SEQUENCE LISTING SUBMITTED ELECTRONICALLY

The official copy of the sequence listing is submitted electronically via EFS-Web as an ASCII formatted sequence listing with a file named "5264_Sequence_Listing.TXT" and is filed concurrently with the specification. The sequence listing contained in this ASCII formatted document is part of the specification and is herein incorporated by reference in its entirety.

FIELD OF THE INVENTION

The present invention relates to novel genes that encode pesticidal polypeptides characterized by pesticidal activity against insect pests. Compositions and methods of the invention utilize the disclosed nucleic acids, and their encoded pesticidal polypeptides, to control plant pests.

BACKGROUND OF THE INVENTION

Insect pests are a major factor in the loss of the world's agricultural crops. For example, armyworm feeding, black cutworm damage, or European corn borer damage can be economically devastating to agricultural producers. Insect pest-related crop loss from European corn borer attacks on field and sweet corn alone has reached about one billion dollars a year in damage and control expenses.

Traditionally, the primary method for controlling insect pest populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including *Lepidoptera, Diptera, Coleoptera, Hemiptera,* and others. *Bacillus thuringiensis* (Bt) and *Bacillus papilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. These genetically engineered crops are now widely used in American agriculture and have provided producers with an environmentally friendly alternative to traditional insect-control methods. While they have proven to be very successful commercially, these genetically engineered, insect-resistant crop plants typically provide resistance to only a narrow range of economically important pests.

Accordingly, there remains a need for new pesticidal proteins with a broader range of insecticidal activity against insect pests, e.g., toxins which are active against a greater variety of insects from the order *Lepidoptera, Coleoptera, Hemiptera,* and others. In addition, there remains a need for biopesticides having improved insecticidal activity, and activity against insects that have developed resistance to existing pesticides and pesticidal proteins.

EMBODIMENTS OF THE INVENTION

1. An isolated insecticidal protein having a structure comprising:
   a) a Domain I, comprising a surface hydrophobic patch and a type 1' β-turn;
   b) a Domain II; and
   c) a Domain III, wherein the surface of Domain II and Domain III comprise a stripe of solvent exposed serine and threonine residues.

2. The isolated insecticidal protein of embodiment 1, wherein Domain I comprises an anti-parallel β-sheet with four short strands and four α-helices designated as helix 1, helix 2, helix 3, and helix 4.

3. The isolated insecticidal protein of any one of embodiments 1-2, wherein the anti-parallel β-sheet of Domain I comprises the C-terminal end of strand 11, strand 12, and the type 1' β-turn joins strand 11 and strand 12.

4. The isolated insecticidal protein of any one of embodiments 1-3, wherein Domain I further comprises a β-hair-pin between helix 2 and helix 3.

5. The isolated insecticidal protein of any one of embodiments 1-4, wherein the surface hydrophobic patch comprises residues from strand 12, helix 2, helix 3, and the type 1' β-turn between strand 11 and strand 12.

6. The isolated insecticidal protein of any one of embodiments 1-5, wherein the hydrophobic patch is about 180-220 Å2.

7. The isolated insecticidal protein of any one of embodiments 1-6, wherein the hydrophobic patch comprises residues corresponding to Phe26, Val48, Pro50, Ile52, Tyr56, Met193, Val202, His205, Tyr206, Phe207, Trp208, Phe209, and Leu210 of SEQ ID NO: 2.

8. The isolated insecticidal protein of any one of embodiments 1-7, wherein Domain 1 comprises residue 1 to about residue 65 and about residue 187 to about residue 223 corresponding to the residues of SEQ ID NO: 2.

9. The isolated insecticidal protein of any one of embodiments 1-8, wherein Domain II comprises five-stranded antiparallel β-sheet (β5/6-β11-β13-β7-β10) patched on one side by an amphipathic β-hairpin stemmed from β2 and β10.

10. The isolated insecticidal protein of any one of embodiments 1-9, wherein Domain II comprises about residue 66 to about residue 79; about residue 104 to about residue 154; about residue 175 to about residue 186; and about residue 224 to about residue 234 corresponding to the residues of SEQ ID NO: 2.

11. The isolated insecticidal protein of any one of embodiments 1-10, wherein Domain III comprises the same five β-strands of Domain II which extend and refold into domain III with a beta-sandwich structure, wherein the three strands β5/6, β11, and β13 make a 180° twist in the middle forming a new 3 stranded β-sheet as one side of a β-sandwich and 67 and 610 spray from the central sheet, twist in middle, and hydrophobically pack against strands β5/6, β11, and β13.

12. The isolated insecticidal protein of any one of embodiments 1-12, wherein Domain III comprises from about residue 80 to about residue 103; about residue 155 to about residue 174; and about residue 235 to about residue 246 corresponding to the residues of SEQ ID NO: 2.

13. The isolated insecticidal protein of any one of embodiments 1-13, wherein the stripe of exposed serine and threonine residues on the surface of Domain II and Domain III comprises: 3 serine and 4 threonine residues in an alternating motif on strand 11, and 3 serine and 2 threonine residues on strand 7.

14. The isolated insecticidal protein of any one of embodiments 1-13, wherein the 3 serine and 4 threonine residues on strand 11 have an average solvent accessibility of about 78.5 Å2 and the 3 serine and 2 threonine residues on strand 7 average solvent exposure of about 59.3 Å2.

15. The isolated insecticidal protein of any one of embodiments 1-14 wherein the protein has an amino acid sequence of SEQ ID NO:2.

16. The isolated insecticidal protein of any one of embodiments 1-14 wherein the protein is encoded by the nucleotide sequence of SEQ ID NO:1.

17. The isolated insecticidal protein of any one of embodiments 1-14 wherein the protein has an amino acid sequence having at least 85% sequence identity to an amino acid sequence of SEQ ID NO:2.

18. An isolated nucleic acid molecule comprising the nucleotide sequence of SEQ ID NO:1.

19. An isolated nucleic acid molecule which encodes a polypeptide comprising the amino acid sequence of SEQ ID NO:2

20. An isolated nucleic acid molecule encoding a protein having insecticidal activity comprising an amino acid sequence characterized by at least 85% sequence identity to an amino acid sequence of any one of embodiments 1-15.

21. An isolated nucleic acid molecule comprising a nucleotide sequence encoding a protein having insecticidal activity comprising an amino acid sequence characterized by at least 85% sequence identity to an amino acid sequence of any one of embodiments 1-15.

22. The isolated nucleic acid molecule of any one of embodiments 18-21, wherein said nucleic acid molecule is a synthetic molecule that has been designed for expression in a plant.

23. A DNA construct comprising the nucleic acid molecule of any one of embodiments 18-22.

24. The DNA construct of any one of embodiments 18-23, further comprising a nucleic acid molecule encoding a heterologous polypeptide.

25. A host cell that contains the DNA construct of any one of embodiments 18-24.

26. The host cell of embodiment 25 that is a bacterial cell.

27. The host cell of embodiment 25 that is a plant cell.

28. A transgenic plant comprising the host cell of embodiment 27.

29. The transgenic plant of embodiment 28, wherein said plant is selected from the group consisting of maize, sorghum, wheat, cabbage, sunflower, tomato, crucifers, peppers, potato, cotton, rice, soybean, sugar beet, sugarcane, tobacco, barley, and oilseed rape.

30. Transformed seed of the plant of embodiment 29, wherein the seed comprise the DNA construct of embodiment 24.

31. A composition comprising the protein of any one of embodiments 1-17.

32. The composition of embodiment 31, wherein said composition is selected from the group consisting of a powder, dust, pellet, granule, spray, emulsion, colloid, and solution.

33. The composition of embodiment 31, wherein said composition is prepared by desiccation, lyophilization, homogenization, extraction, filtration, centrifugation, sedimentation, or concentration of a culture of micor-organisms.

34. A method for controlling a pest population comprising contacting said population with an insecticidally-effective amount of the protein of embodiment 31.

35. A method for killing a pest comprising contacting said pest with, or feeding to said pest, an insecticidally-effective amount of the protein of embodiment 31.

36. A method for producing a polypeptide with insecticidal activity, comprising culturing the host cell of embodiment 26 under conditions in which a nucleic acid molecule encoding the polypeptide is expressed, said polypeptide being selected from the group consisting of:
(a) a polypeptide comprising the amino acid sequence of SEQ ID NO:2 or 10;
(b) a polypeptide that is encoded by the nucleotide sequence of SEQ ID NO:1 or 9; and
(c) a polypeptide sequence having at least 85% sequence identity to a polypeptide sequence of (a) or (b).

37. A plant having stably incorporated into its genome a DNA construct comprising a nucleotide sequence that encodes a protein having insecticidal activity, wherein said nucleotide sequence is selected from the group consisting of:
(a) a nucleic acid molecule comprising the nucleotide sequence of SEQ ID NO: 1 or 9;
(b) a nucleic acid molecule which encodes a polypeptide comprising the amino acid sequence of SEQ ID NO:2 or 10; and
(c) a nucleotide sequence encoding a protein having pestical activity comprising an amino acid sequence characterized by at least 85% sequence identity to an amino acid sequence of (b); wherein said nucleotide sequence is operably linked to a promoter that drives expression of a coding sequence in a plant cell.

38. A method for protecting a plant from a pest, comprising introducing into said plant or cell thereof at least one expression vector comprising a nucleotide sequence that encodes a insecticidal polypeptide, wherein said nucleotide sequence is selected from the group consisting of:
(a) a nucleic acid molecule comprising the nucleotide sequence of SEQ ID NO:1 or 9;
(b) a nucleic acid molecule which encodes a polypeptide comprising the amino acid sequence of SEQ ID NO:2 or 10;
(e) a nucleotide sequence encoding a protein having insecticidal activity comprising an amino acid sequence characterized by at least 85% sequence identity to an amino acid sequence of (b); and
(f) a nucleotide sequence encoding a protein having insecticidal activity comprising an amino acid sequence characterized by at least 85% sequence identity to an amino acid sequence of (b).

39. The method of embodiment 38, wherein said plant produces an insecticidal protein having insecticidal activity against European Corn Borer, Fall Armyworm, Corn Earworm, Black Cutworm, Soybean Looper, Velvetbean Caterpillar, Western Corn Rootworm, *Lygus* spp. and Stinkbug.

BRIEF DESCRIPTION OF THE FIGURES

FIG. 1 shows an alignment of MP467 (SEQ ID NO: 2) as the "Query" sequence with a hydralysin protein from Hydra viridissima (SEQ ID NO: 4) as the "Sbjct" sequence.

FIG. 2 shows an alignment of MP467 (SEQ ID NO: 2) as the "Query" sequence with a parasporin 2/Cry46Aa protein from *Bacillus thuringiensis* (SEQ ID NO: 10) as the "Sbjct" sequence.

FIG. 3 shows a sequence alignment of Beta hairpin structures with alternating residues from MP467 (SEQ ID NO: 2) and homologs: .Parasporin-2 from *Bacillus thuringiensis* (Ps2—SEQ ID NO: 15); Hydralysin from Cnidaria (Hdr—SEQ ID NO: 16); Alpha-toxin from *Clostridium septicum* (Apt—SEQ ID NO: 17); Aerolvsin from *Aerimonas*(Aer—SEQ ID NO: 18); ϵ-toxin from *Clostridium perfrinqens* (Epn—SEQ ID NO: 19); Hemolytic lectin from *Laetiporus sulphureus* (LSL—SEQ ID NO: 20); Enterotoxin from *Clostridium perfrinqens* (CPE—SEQ ID NO: 21); and Alpha-hemolysin from *Staphylococcus Aureus* (Aph—SEQ ID NO: 22).

DETAILED DESCRIPTION OF THE INVENTION

Figure 4:
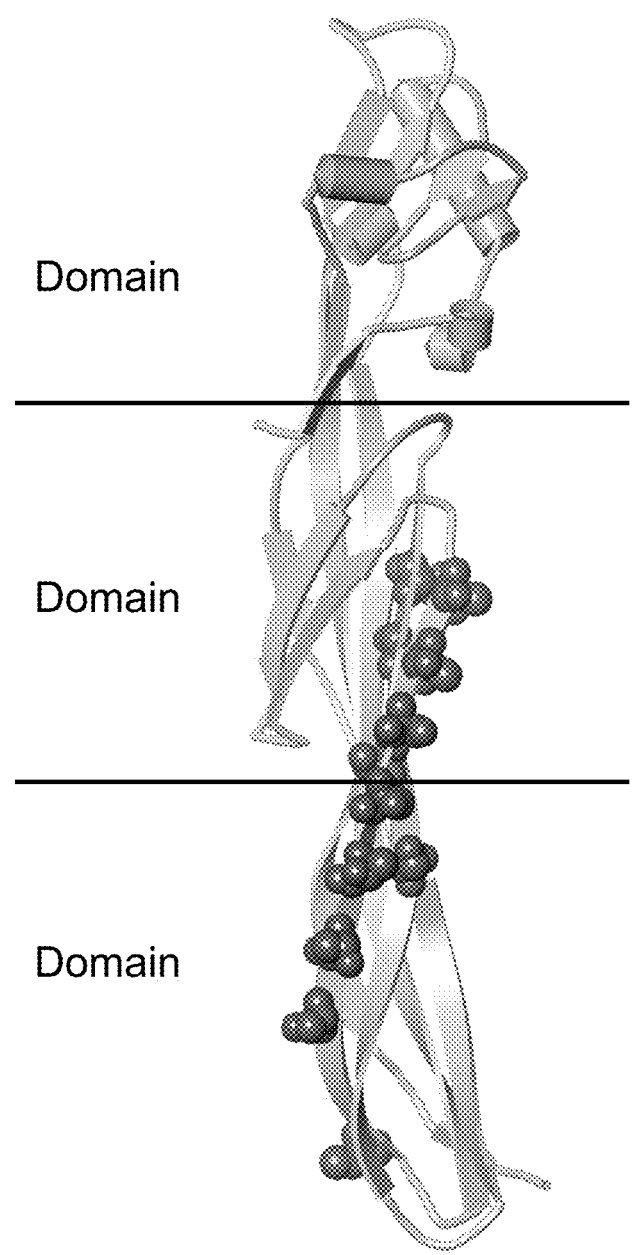
FIG. 4 shows the overall 3 Domain structure of MP467 and Cry 46A

The embodiments of the invention are drawn to compositions and methods for controlling insect pests, particularly plant pests. More specifically, the isolated nucleic acid of the embodiments, and fragments and variants thereof, comprise nucleotide sequences that encode pesticidal polypeptides (e.g., proteins). The disclosed pesticidal proteins are biologically active (e.g., pesticidal) against insect pests such as, but not limited to, insect pests of the order *Lepidoptera*, *Coleoptera*, and *Hemiptera*. Insect pests of interest include, but are not limited to: *Ostrinia nubilalis* (European Corn Borer), *Spodoptera frugiperda* (Fall Armyworm), *Helicoverpa zea* Boddie (Corn Earworm), *Agrotis ipsilon* Hufnagel (Black Cutworm), *Pseudoplusia includens* Walker (Soybean Looper), *Anticarsia gemmatalis* Hübner (Velvetbean Caterpillar), *Diabrotica virgifera virgifera* (Western Corn Rootworm), Southern Corn Rootworm (*Diabrotica* spp.), Northern Corn Rootworm (*Diabrotica* spp.), Mexican Bean Beetle (*Epilachna varivestis* Mulsant), Stinkbugs (family Pentatomidae) and *Lygus* spp.

The compositions of the embodiments comprise isolated nucleic acids, and fragments and variants thereof that encode pesticidal polypeptides, expression cassettes comprising nucleotide sequences of the embodiments, isolated pesticidal proteins and variants and fragments thereof, and pesticidal compositions.

The embodiments further provide isolated pesticidal (e.g., insecticidal) polypeptides encoded by either a naturally-occurring or modified nucleic acid of the embodiments. More specifically, the embodiments provide polypeptides comprising an amino acid sequence set forth in SEQ ID NO: 2 and 10, and the polypeptides encoded by nucleic acids described herein, for example those set forth in SEQ ID NO: 1 and 9, and fragments and variants thereof.

Some embodiments provide modified pesticidal polypeptides characterized by improved insecticidal activity relative to the pesticidal activity of the corresponding wild-type protein. The embodiments further provide plants and microorganisms transformed with these novel nucleic acids, and methods involving the use of such nucleic acids, pesticidal compositions, transformed organisms, and products thereof in controlling insect pests.

The nucleic acids and nucleotide sequences of the embodiments may be used to transform any organism to produce the encoded pesticidal proteins. Methods are provided that involve the use of such transformed organisms to control plant pests. The nucleic acids and nucleotide sequences of the embodiments may also be used to transform organelles such as chloroplasts (McBride et al. (1995) *Biotechnology* 13: 362-365; and Kota et al. (1999) *Proc. Natl. Acad. Sci. USA* 96: 1840-1845).

The embodiments further relate to the identification of fragments and variants of the naturally-occurring coding sequence that encode biologically active pesticidal proteins. The nucleotide sequences of the embodiments find direct use in methods for controlling pests. Accordingly, the embodiments provide new approaches for controlling insect pests that do not depend on the use of traditional, synthetic chemical insecticides. The embodiments involve the discovery of naturally-occurring, biodegradable pesticides and the genes that encode them.

The embodiments further provide fragments and variants of the naturally occurring coding sequence that also encode biologically active (e.g., pesticidal) polypeptides. The nucleic acids of the embodiments encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The embodiments further provide mutations which confer improved or altered properties on the polypeptides of the embodiments. See, e.g., copending U.S. application Ser. No. 10/606,320, filed Jun. 25, 2003, and Ser. No. 10/746,914, filed Dec. 24, 2003.

In the description that follows, a number of terms are used extensively. The following definitions are provided to facilitate understanding of the embodiments.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above terms are more fully defined by reference to the specification as a whole.

By "pesticidal toxin" or "pesticidal protein" is intended a protein that has toxic activity against one or more pests, including, but not limited to, members of the *Lepidoptera, Diptera, Hemiptera*, and *Coleoptera* orders, or the Nematoda phylum, or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

In some embodiments the polypeptides of the invention include amino acid sequences deduced from the full-length nucleic acid sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Terms used to describe the protein structural motifs and secondary structures herein have their standard meaning in the art. See for example: Creighton, Thomas A., *Proteins: Structures and Molecular Properties*, W.H. Freeman; Second ed. (1992); Kabsch, et. al., Dictionary of Protein Secondary Structure, *Biopolymers*, Vol. 22, 2577-2637 (1983).

As used herein, the term "improved insecticidal activity" or "improved pesticidal activity" refers to an insecticidal polypeptide of the embodiments that has enhanced insecticidal activity relative to the activity of its corresponding wild-type protein, and/or an insecticidal polypeptide that is effective against a broader range of insects, and/or an insecticidal polypeptide having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type insecticidal polypeptide determined against the same insect.

For example, an improved pesticidal or insecticidal activity is provided where a wider or narrower range of insects controlled by the polypeptide relative to the range of insects that is affected by a wild-type toxin. A wider range of control may be desirable where versatility is desired, while a narrower range may be desirable where, for example, beneficial insects might otherwise be impacted by use or presence of the toxin. While the embodiments are not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

Changes can be made to the polypeptides of the invention that confer other desirable physical or biological characteristics, including but not limited to: reduced hemolytic activity, altered sensitivity to pepsin, trypins, chymotrypsins, and other proteases. Alterations that can be made without a negative impact on the pesticidal or insecticidal activity of the protein are encompassed by the invention.

For example, conservative amino acid substitutions may be made at one or more predicted, nonessential, amino acid residues. A "nonessential" amino acid residue is a residue that can be altered from the wild-type sequence of a polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity, except as otherwise noted herein. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, J Mol Biol. 157(1): 105-32, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, Ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making such changes, the substitution of amino acids whose hydropathic indices are within .+2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different polypeptide coding regions can be used to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272: 336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered polypeptides. Domains may be swapped between pesticidal polypeptides, resulting in hybrid or chimeric toxins with improved pesticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266: 17954-17958; Schnepf, et al., (1990) *J. Biol. Chem.* 265: 20923-20930; Rang, et al., 91999) *Appl. Environ. Microbiol.* 65:2918-2925).

Amino acid sequences homologous to MP467 (SEQ ID NO:2) were identified by similarity search on the non-redundant database (nr) of National Center for Bioinformatics Information (NCBI) using BLAST and PSI-BLAST. Hidden Markov Model profile method (HMMER3) was also used to expand the membership search through two PFAM families, aerolysin and ETX_MT2 (Clostridium ϵ-toxin and *Bacillus* mosquitocidal toxin). A total of 485 sequences in the NCBI non-redundant database have a low, but detectable, similarity to the mp467s (<70%). After redundancy reduction in which two sequences are clustered as one if they are with 95% identical over 95% length, 333 unique sequences are identified. The homologous proteins are found in all kingdoms of life although vast majority of them are bacterial toxins such as aerolysin from *Aeromonas*, alpha-toxin from *Clostridium septicum*, ϵ-toxin form *Clostridium perfringens*, parasporin-2 (PS2) from *Bacillus thuringiensis*.

A hydralysin from *Hydra viridissima* showed 67% sequence similarity to MP467 when aligned over the entire length of MP467 (see FIG. 1, and SEQ ID NO:4). This protein demonstrated weak insecticidal activity with a similar spectrum.

A protein from *Bacillus thuringiensis* showed 57% sequence similarity MP467 when aligned over the entire length of MP467 (see FIG. 2 and SEQ ID NO: 6). Early publications named some of these proteins parasporins, to distinguish them from the insecticidal Cry proteins. The parasporins are still thought to be non-insecticidal. Later, the parasporins adopted the Cry protein nomenclature, hence multiple names for the same protein. As used herein, "parasporin-2Aa" "PS2" and "Cry46Aa" may be used interchangeably and refer to SEQ ID NO: 10 and its functional variants and fragments. This protein demonstrated good insecticidal activity over a broad range (See Example 2).

Two similar proteins from *B. thuringiensis*, MP543 and 544 showing similar homology to MP467 had no insecticidal activity (SEQ ID NOs: 6 and 8).

In addition, hydralysins from *Cnidaria*, hemolytic lectin from the parasitic mushroom *Laetiporus sulphureus*, and enterolobin produced by the seeds of the Brazilian tree are also in this list.

One aspect pertains to isolated or recombinant nucleic acid molecules comprising nucleic acid sequences encoding the polypeptides of the invention or biologically active portions thereof, as well as nucleic acid molecules sufficient for use as hybridization probes to identify nucleic acid molecules encoding proteins with regions of sequence homology. As used herein, the term "nucleic acid" is intended to include DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

An "isolated" or "recombinant" nucleic acid molecule (or DNA) is used herein to refer to a nucleic acid sequence (or DNA) that is no longer in its natural environment, for example in an in vitro or in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecule encoding a polypeptide of the invention can contain less than about 5 kb, 4 kb, 3 kb, 2 kb, 1 kb, 0.5 kb, or 0.1 kb of nucleic acid sequences that naturally flank the nucleic acid molecule in genomic DNA of the cell from which the nucleic acid is derived.

A variety of polynucleotides that encode a polypeptide of the invention or related proteins are contemplated. Such polynucleotides are useful for production of polypeptides in host cells when operably linked to suitable promoter, transcription termination and/or polyadenylation sequences. Such polynucleotides are also useful as probes for isolating homologous or substantially homologous polynucleotides that encode polypeptides of the invention or related proteins.

As used herein, the term "mutant nucleotide sequence" or "mutation" or "mutagenized nucleotide sequence" connotes a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a mutant insecticidal toxin showing improved or decreased insecticidal activity, or an amino acid sequence which confers improved or decreased insecticidal activity on a polypeptide containing it. As used herein, the term "mutant" or "mutation" in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A mutant polypeptide shows improved or decreased insecticidal activity, or represents an amino acid sequence which confers improved insecticidal activity on a polypeptide containing it. Thus, the term "mutant" or "mutation" refers to either or both of the mutant nucleotide sequence and the encoded amino acids. Mutants may be used alone or in any compatible combination with other mutants of the embodiments or with other mutants. A "mutant polypeptide" may conversely show a decrease in insecticidal activity. Where more than one mutation is added to a particular nucleic acid or protein, the mutations may be added at the same time or sequentially; if sequentially, mutations may be added in any suitable order.

Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

In this manner, embodiments of the invention provide amino acid and nucleic acid sequences comprising a variety of mutations, such as for example, mutagenesis of the hydrophobic patch that retain or exceed the pesticidal activity of the wild type protein.

Compositions of the embodiments include nucleic acids, and fragments and variants thereof, that encode pesticidal polypeptides. In particular, the embodiments provide for isolated nucleic acid molecules comprising nucleotide sequences encoding the amino acid sequence shown in SEQ ID NO: 2, or the nucleotide sequences encoding said amino acid sequence, for example the nucleotide sequence set forth in SEQ ID NO: 1, insecticidal fragments and variants thereof and insecticidal variants shown in Table 6.

Fragments and variants of the nucleotide and amino acid sequences and the polypeptides encoded thereby are also encompassed by the embodiments. As used herein the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. Thus, it is acknowledged that some of the polynucleotide and amino acid sequences of the embodiments can correctly be referred to as both fragments and mutants.

It is to be understood that the term "fragment," as it is used to refer to nucleic acid sequences of the embodiments, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a nucleotide sequence of the embodiments that encodes a biologically active portion of a pesticidal protein of the embodiments will encode at least 15, 25, 30, 50, 100, 200 or 300 contiguous amino acids, or up to the total number of amino acids present in a pesticidal polypeptide of the embodiments (for example, 258 amino acids for SEQ ID NO: 2). Thus, it is understood that the embodiments also encompass polypeptides that are fragments of the exemplary pesticidal proteins of the embodiments and having lengths of at least 15, 25, 30, 50, 100, 200, or 300 contiguous amino acids, or up to the total number of amino acids present in a pesticidal polypeptide of the embodiments. Fragments of a nucleotide sequence of the embodiments that are useful as hybridization probes or PCR primers generally need not encode a biologically active portion of a pesticidal protein. Thus, a fragment of a nucleic acid of the embodiments may encode a biologically active portion of a pesticidal protein, or it may be a fragment that can be used as a hybridization probe or PCR primer using methods disclosed herein. A biologically active portion of a pesticidal protein can be prepared by isolating a portion of one of the nucleotide sequences of the embodiments, expressing the encoded portion of the pesticidal protein (e.g., by recombinant expression in vitro), and assessing the activity of the encoded portion of the pesticidal protein.

Nucleic acids that are fragments of a nucleotide sequence of the embodiments comprise at least 16, 20, 50, 75, 100, 150, 200, 250, 300, 350, 400, 450, 500, 600, 700, or 800 nucleotides, or up to the number of nucleotides present in a nucleotide sequence disclosed herein (for example, 777 nucleotides for SEQ ID NO: 1). Particular embodiments envision fragments derived from (e.g., produced from) a first nucleic acid of the embodiments, wherein the fragment encodes a truncated toxin characterized by pesticidal activity. Truncated polypeptides encoded by the polynucleotide fragments of the embodiments are characterized by pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' end of the native or corresponding full-length coding sequence.

The term "variants" is used herein to refer to substantially similar sequences. For nucleotide sequences, conservative variants include those sequences that, because of the degeneracy of the genetic code, encode the amino acid sequence of one of the pesticidal polypeptides of the embodiments. Naturally occurring allelic variants such as these can be identified with the use of well-known molecular biology techniques, such as, for example, polymerase chain reaction (PCR) and hybridization techniques as outlined herein.

Variant nucleotide sequences also include synthetically derived nucleotide sequences, such as those generated, for example, by using site-directed mutagenesis but which still encode a pesticidal protein of the embodiments, such as a mutant toxin. Generally, variants of a particular nucleotide sequence of the embodiments will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the embodiments may differ from that sequence by as few as 1-15 nucleotides, as few as 1-10, such as 6-10, as few as 5, as few as 4, 3, 2, or even 1 nucleotide.

Variants of a particular nucleotide sequence of the embodiments (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO: 2 are disclosed. Percent sequence identity between any two polypeptides can be calculated using sequence alignment programs described elsewhere herein using default parameters. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook". See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138: 267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, "% form" is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Washes are typically performed at least until equilibrium is reached and a low background level of hybridization is achieved, such as for 2 hours, 1 hour, or 30 minutes.

$T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook. Thus, isolated sequences that encode a protein of the embodiments and hybridize under stringent conditions to the sequences disclosed herein, or to fragments thereof, are encompassed by the embodiments.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Center for Biotechnology Information website on the world wide web at ncbi.hlm.nih.gov. Alignment may also be performed manually by inspection.

Unless otherwise stated, sequence identity/similarity values provided herein refer to the value obtained using GAP Version 10 using the following parameters: identity and % similarity for a nucleotide sequence using GAP Weight of 50 and Length Weight of 3, and the nwsgapdna.cmp scoring matrix; % identity and similarity for an amino acid sequence using GAP Weight of 8 and Length Weight of 2, and the BLOSUM62 scoring matrix; or any equivalent program thereof. The term "equivalent program" as used herein refers to any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%. 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures, and the like.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, "operably linked" means that the nucleic acid sequences being linked are contiguous and, where necessary to join two protein coding regions, contiguous and in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the insecticidal sequence to be under the transcriptional regulation of the regulatory regions. The DNA construct may additionally contain selectable marker genes.

The DNA construct may include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes. See, for example, U.S. Pat. Nos. 5,380, 831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes or constructs may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette or construct, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize 1n2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803;

Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glb-1 are endosperm-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette or construct will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481; and U.S. application Ser. Nos. 10/004,357; and 10/427,692); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in The Operon, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) *Ph.D. Thesis*, University of Heidelberg; Reines et al. (1993) *Proc. Natl. Acad. Sci. USA*

90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) *Ph.D. Thesis*, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the embodiments.

A further embodiment relates to a transformed organism such as an organism selected from the group consisting of plant and insect cells, bacteria, yeast, baculoviruses, protozoa, nematodes, and algae. The transformed organism comprises: a DNA molecule of the embodiments, an expression cassette comprising the said DNA molecule, or a vector comprising the said expression cassette, which may be stably incorporated into the genome of the transformed organism.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6: 923-926); and Lecl transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the Cry toxin protein or variants and fragments thereof directly into the plant or the introduction of the Cry toxin transcript into the plant. Such methods include, for example, microinjection or particle bombardment. See, for example, Crossway et al. (1986) *Mol. Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cry toxin polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus*, *B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

In certain embodiments the nucleic acid sequences of the embodiments can be stacked with any combination of polynucleotide sequences of interest in order to create plants with a desired phenotype. For example, the polynucleotides of the embodiments may be stacked with any other polynucleotides encoding polypeptides having pesticidal and/or insecticidal activity, such as Bt toxic proteins (described in U.S. Pat. Nos. 5,366,892; 5,747,450; 5,736,514; 5,723,756; 5,593,881; and Geiser et al. (1986) *Gene* 48:109), pentin (described in U.S. Pat. No. 5,981,722) and the like. The combinations generated can also include multiple copies of any one of the polynucleotides of interest. The polynucleotides of the embodiments can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,049); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) Science 266:789; Martin et al. (1993) Science 262: 1432; and Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene as disclosed in U.S. application Ser. Nos. 10/004,357; and 10/427, 692); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170: 5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a nucleotide sequence encoding a pesticidal protein of the embodiments may be treated with a seed protectant coating comprising a seed treatment compound, such as, for example, captan, carboxin, thiram, methalaxyl, pirimiphos-methyl, and others that are commonly used in seed treatment. In one embodiment, a seed protectant coating comprising a pesticidal composition of the embodiments is used alone or in combination with one of the seed protectant coatings customarily used in seed treatment.

It is recognized that the genes encoding the pesticidal proteins can be used to transform insect pathogenic organisms. Such organisms include baculoviruses, fungi, protozoa, bacteria, and nematodes.

A gene encoding a pesticidal protein of the embodiments may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes,* fungi, particularly yeast, e.g., *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) *Molecular Cloning: A Laboratory Manual*, ed. Maniatis et al. (Cold Spring Harbor Laboratory Press, Cold Spring Harbor, N.Y.), hereinafter "Sambrook II"; Davis et al., eds. (1980) *Advanced Bacterial Genetics* (Cold Spring Harbor Laboratory Press), Cold Spring Harbor, N.Y.; and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia*, *Erwinia*, *Shigella*, *Salmonella*, and *Proteus*; Bacillaceae; Rhizobiaceae, such as *Rhizobium*; Spirillaceae, such as *photobacterium*, *Zymomonas*, *Serratia*, *Aeromonas*, *Vibrio*, *Desulfovibrio*, *Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula*, *Aureobasidium*, *Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa*, *P. fluorescens*), *Erwinia* spp., and *Flavobacterium* spp., and other such organisms, including Bt, *E. coli, Bacillus subtilis*, and the like.

Genes encoding the pesticidal proteins of the embodiments can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the embodiments can be introduced into a root-colonizing *Bacillus cereus* by standard methods known in the art.

Genes encoding pesticidal proteins can be introduced, for example, into the root-colonizing *Bacillus* by means of electrotransformation. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria, such as *E. coli*, for example. Advantages of having pesticidal proteins secreted are: (1) avoidance of potential cytotoxic effects of the pesticidal protein expressed; and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Pesticidal proteins of the embodiments can be fermented in a bacterial host and the resulting bacteria processed and used as a microbial spray in the same manner that Bt strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express Bt toxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide.

These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EPA 0192319, and the references cited therein.

In the embodiments, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal composition(s) that is, for example, a suspension, a solution, an emulsion, a dusting powder, a dispersible granule or pellet, a wettable powder, and an emulsifiable concentrate, an aerosol or spray, an impregnated granule, an adjuvant, a coatable paste, a colloid, and also encapsulations in, for example, polymer substances. Such formulated compositions may be prepared by such conventional means as desiccation, lyophilization, homogenization, extraction, filtration, centrifugation, sedimentation, or concentration of a culture of cells comprising the polypeptide.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the pesticidal proteins produced by the bacterial strains of the embodiments include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acyl-sarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphthalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the embodiments can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins of the embodiments, can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The compositions (including the transformed microorganisms and pesticidal proteins of the embodiments) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the pesticidal protein and/or transformed microorganisms of the embodiments may be mixed with grain to protect the grain during storage. It is generally important to obtain good control of pests in the early stages of plant growth, as this is the time when the plant can be most severely damaged. The compositions of the embodiments can conveniently contain another insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, an herbicide, an insecticide, a fertilizer, an inert carrier, and dead cells of a *Bacillus* strain or transformed microorganism of the embodiments.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household and stored product pests. Insect pests include insects selected from the orders *Coleoptera, Diptera*, Hymenoptera, *Lepidoptera*, Mallophaga, Homoptera, *Hemiptera*, Orthoptera, Thysanoptera, Dermaptera, Isoptera, Anoplura, Siphonaptera, Trichoptera, etc., particularly *Lepidoptera*.

Larvae and adults of the order *Coleoptera* include weevils from the families Anthribidae, Bruchidae, and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles, and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith & Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (corn flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Larvae of the order *Lepidoptera* include, but are not limited to, armyworms, cutworms, loopers, and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other Archips species, *Adoxophyes orana* Fischer von Rosslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermuller (European grape vine moth); *Spilonota ocellana* Denis & Schiffermuller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order *Lepidoptera* include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Meneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Meneville (grapeleaf skeletonizer); *Hemileuca oliviae* Cockrell (range caterpillar); *Hyphantria cunea* Drury (fall webworm); *Keiferia lycoper-* sicella Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Adults and immatures of the order *Diptera* include: leafminers such as *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (frit flies); maggots (including, but not limited to: *Delia platura* Meigen (seedcorn maggot); *D. coarctata* Fallen (wheat bulb fly); and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Adults and nymphs of the orders *Hemiptera* and *Homoptera* include insects such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae, Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae, and red bugs and cotton stainers from the family Pyrrhocoridae.

Agronomically important members from the order *Homoptera* further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid); and *T. citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (whitebacked planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species from the order *Hemiptera* include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Insects included in the order *Hemiptera* include: *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp.; and *Cimicidae* spp.

Adults and larvae of the order Acari (mites) include: *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura include *Lepisma saccharina* Linnaeus (silverfish); *Thermobia domestica* Packard (firebrat). Additional arthropod pests include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede).

TABLE 1

Insect pests and their abbreviations as used herein:

| | |
|---|---|
| ECB | European corn borer (*Ostrinia nubilalis*) |
| FAW | Fall armyworm (*Spodoptera frugiperda*) |
| CEW | Corn earworm (*Helicoverpa zea* Boddie) |
| BCW | Black cutworm (*Agrotis ipsilon* Hufnagel) |
| SBL | Soybean looper (*Pseudoplusia includens* Walker) |
| VBC | Velvetbean Caterpillar (*Anticarsia gemmatalis* Hübner) |
| WCRW | Western Corn Rootworm (*Diabrotica virgifera virgifera*) |
| Stinkbug | *Halyomorpha halys, Acrosternum hilare*, other Pentatomidae agricultural pests |
| *Lygus* | *Lygus Hesperus, L. elisus* |

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C.D.S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of *cereus, firmus, megaterium, pumilis, sphaericus, subtilis* and/or *thuringiensis*), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio)benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

In some embodiments methods are provided for killing or controlling an insect pest, comprising contacting the insect pest, either simultaneously or sequentially, with an insecticidally-effective amount of a recombinant polypeptide of the invention. In some embodiments methods are provided for killing an insect pest, comprising contacting the insect pest with an insecticidally-effective amount of a recombinant pesticidal protein of SEQ ID NO: 2 and/or protein of SEQ ID NO: 10 or a variant thereof.

As used herein, "controlling a pest population" or "controls a pest" refers to any effect on a pest that results in limiting the damage that the pest causes. Controlling a pest includes, but is not limited to: killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of a recombinant polypeptide of the invention. In some embodiments methods are provided for controlling an insect pest population resistant to a pesticidal protein, comprising contacting the insect pest population with an insecticidally-effective amount of a recombinant pesticidal protein of SEQ ID NO: 2 and/or protein of SEQ ID NO: 10 or a variant thereof.

In some embodiments methods are provided for protecting a plant from an insect pest, comprising expressing in the plant or cell thereof a recombinant polynucleotide encoding a polypeptide of the invention. In some embodiments methods are provided for protecting a plant from an insect pest, comprising expressing in the plant or cell thereof a recombinant polynucleotide encoding pesticidal protein of SEQ ID NO: 2 and/or protein of SEQ ID NO: 10 or variants thereof.

In some embodiments, a pest population may be controlled by means of a composition comprising the polypeptides of the invention in a pesticidally-effective amount in a form including, but not limited to: a powder, dust, pellet, granule, spray, emulsion, colloid, or solution and a suitable carrier.

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, and the like.

Provided are methods of controlling insect infestation(s) in a transgenic plant that promote insect resistance management, comprising expressing in the plant at least two different insecticidal proteins having different modes of action.

In some embodiments the methods of controlling insect infestation in a transgenic plant and promoting insect resistance management, at least one of the insecticidal proteins comprise a polypeptide of the invention insecticidal to insects.

In some embodiments the methods of controlling insect infestation in a transgenic plant and promoting insect resistance management, at least one of the insecticidal proteins comprises a protein of SEQ ID NO:2 and/or protein of SEQ ID NO: 10 or variants thereof, insecticidal to insects in the order *Lepidoptera* and/or *Coleoptera*.

In some embodiments the methods of controlling insect infestation in a transgenic plant and promoting insect resistance management, comprise expressing in the transgenic plant a polypeptide of the invention and an insecticidal Cry protein having different modes of action.

Also provided are methods of reducing the likelihood of emergence of insect resistance to transgenic plants by expressing in the plants insecticidal proteins to control the insect species, comprising expression of a polypeptide of the invention in combination with a second insecticidal protein to the insect species having different modes of action.

Also provided are means for effective insect resistance management of transgenic plants, comprising co-expressing at high levels in the plants, two or more insecticidal proteins toxic to *Lepidoptera* and/or *Coleoptera* insects but each exhibiting a different mode of effectuating its killing activity, wherein the two or more insecticidal proteins comprise a polypeptide of the invention and a Cry protein.

In addition, methods are provided for obtaining regulatory approval for planting or commercialization of plants expressing insecticidal proteins, comprising the step of referring to, submitting or relying on insect assay binding data showing that the polypeptides of the invention do not compete with binding sites for Cry proteins in such insects.

The following examples are offered by way of illustration and not by way of limitation.

TABLE 2

Table of Sequences

| SEQ ID NO | Gene Name | Organism | Sequence Type |
|---|---|---|---|
| 1 | MP467S | Bacillus sphaericus | NT |
| 2 | " | " | AA |
| 3 | hydralysin-2 | Hydra vulgaris | NT |
| 4 | " | " | AA |
| 5 | 543S | B.thuringiensis | NT |
| 6 | " | " | AA |
| 7 | 544S | B. thuringiensis | NT |
| 8 | " | " | AA |
| 9 | Cry46Aa/(parasporin-2Aa) | B. thuringiensis | NT |
| 10 | " | " | AA |
| 11 | Cry46Ab/(parasporin 2Ab) | B. thuringiensis | NT |
| 12 | " | " | AA |
| 13 | Hydrophobic patch motif | Artificial sequence | AA |

EXPERIMENTALS

Example 1

Isolation and Modeling of MP467 and Cry46Aa

Insecticidal protein MP467 was obtained from a screen of proteins derived from Bacillus sphaericus strain AM1922.

MP467 homologous sequences were identified by similarity search on the non-redundant database (nr) of National Center for Bioinformatics information (NCBI) using BLAST and PSI-BLAST, Hidden Markov Model profile method (HMMER3) was also used to expand the membership search through two PFAM aerolysin and ETX_MT2 (Clostridium ε-toxin and Bacillus mosquitocidal toxin). Total 485 sequences in the NCBI non-redundant database have a detectable similarity to the mp467s. After redundancy reduction in which two sequences are clustered as one if they are with 95% identical over 95% length, 333 unique sequences are identified. The homologous proteins are found in all kingdoms of life although vast majority of them are bacterial toxins such as aerolysin from Aeromonas (genbank accession: YP_001143607), alpha-toxin from Clostridium septicum (ABD65254), E-toxin form Clostridium perfringens (CAA43104), parasporin-2 (PS2) from Bacillus thuringiensis (BAC79010). In addition, hydralysins from Cnidaria (XP_002158854), hemolytic lectin from the parasitic mushroom Laetiporus sulphureus (BAC78489), and enterolobin produced by the seeds of the Brazilian tree (P81007) See Table 8.

Structural modeling revealed that MP467 has a significant structural similarity to a well-studied aerolysin family.

The structure of MP467 was modeled using standard homology modeling techniques available within the Discovery Studio 3.5© software. (Copyright 2005-12 Accelrys Software) In brief, the MP467 amino acid sequence was used as the query sequence to BLAST against the available structures in the Protein Databank (PBD). The top scoring BLAST hit was parasporin-2 from Bacillus thuringiensis (PDB ID 2ZTB) with an overall sequence identity of 42% covering 245 amino acids of the query sequence and an E-value of 4.0674e-45. The parasporin-2 structure (2ztb) was used as the structural template for the MP467 sequence. During the homology modeling procedure 20 models for MP467 were generated, energy minimized with high optimization setting (Discovery Studio 3.5©) and scored. The lowest energy model was used in the following structural analysis of MP467

Figure 5:
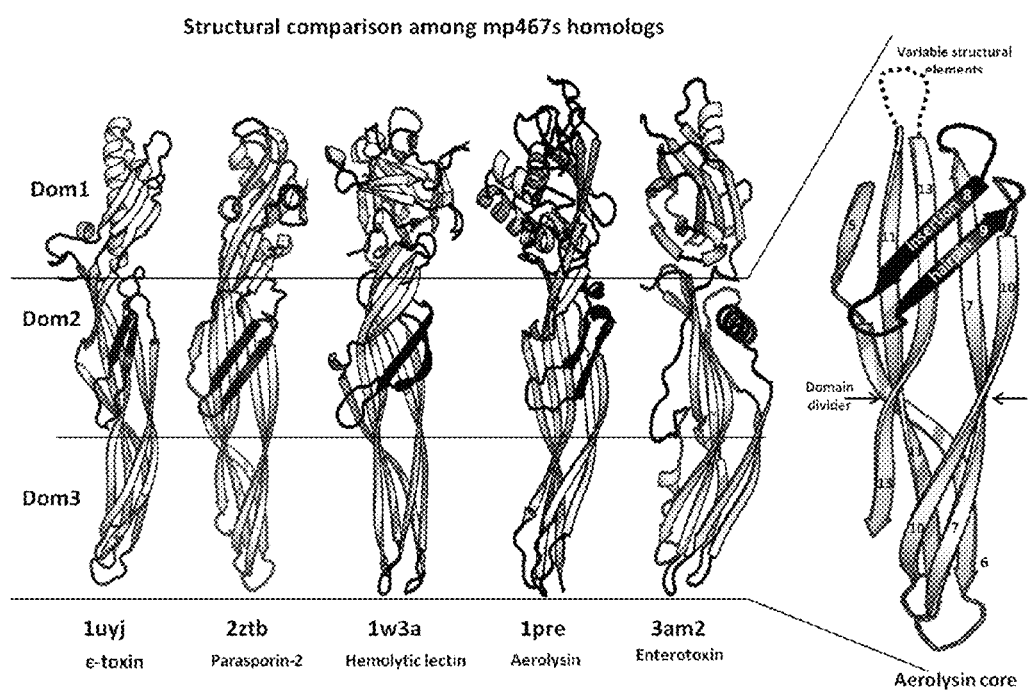
FIG. 5 shows structural comparisons between MP467 homologs.

The overall structure of modeled MP467 shares a high degree of similarity to the parasporin-2 structure (2ztb) the largest differences resulting from a two residue deletion in the loop connecting β11 and β12 (Akiba, 2009) Briefly the model for MP467 is comprised of an elongated β-strand structure (approximately 113 Å×18 Å×25 Å) aligned with its long axis, similar to aerolysin-type β-pore-forming toxins (Szczesny et al., 2011). According to the areolysin structure convention, the PS2 structure (2ztb) consists of three structural domains with the two longest beta strands (β4 and β5) running through the entire three domains (FIGS. 4 and 5). In LSL, β4 and β5 are short and only cover the domain 2 and 3 while they have a large subdomain extension encompassing half of the receptor binding domain in aerolysin. In order to better refine the structure core and reveal more structural homologues, the variable elements (residue 52:116 and 240-274, domain I) were removed from PS2 structure (2ztb) and structural similarity was determined using the Dali algorithm (Holm L, Rosenström P (2010) Dali server: conservation mapping in 3D. Nucl. Acids Res. 38, W545-549). The core domain is similar to ε-toxin (PDB:1 uyj, Cole et al. 2004), hemolytic lectin from mushroom (1w3a, 1w3f, and 1w3g, Mancheño et a;. 2005), aerolysin from various sources (3g4o, 1pre, etc, Rossjohn et al., 1998), and enterotoxin (2xh6 and amx2, Kitadokoro et al., 2011), consistent with the sequence comparison. Although these toxins have drastically different Domain I structures likely reflecting their distinct target specificity, they exhibit the same general topology in Domain II and Domain III establishing their evolutionary and functional relevancy.

Figure 6:
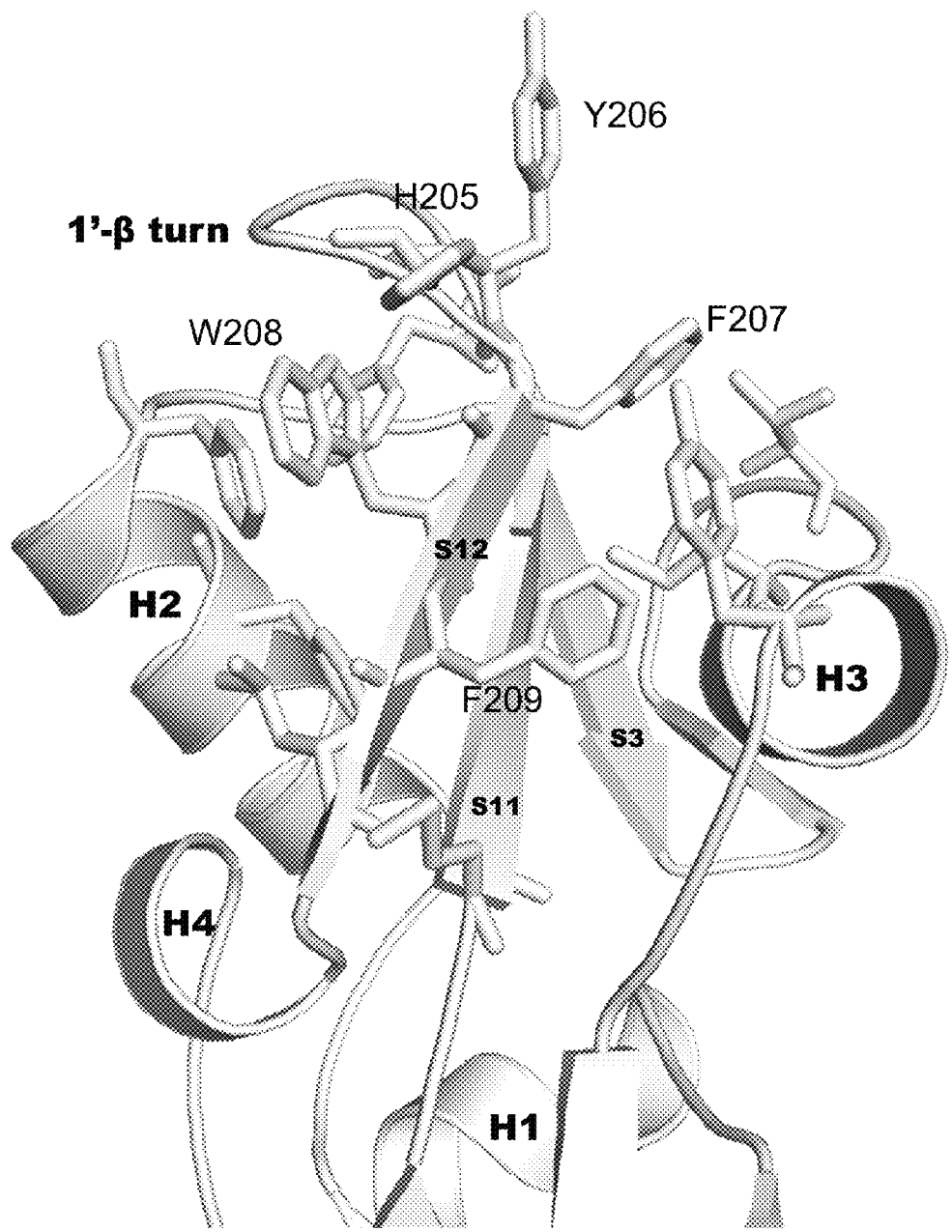
FIG. 6 shows the detail of Domain 1 of MP467.

Domain I of MP467 is comprised of residues 1 to 65, and residues 187 to 223 (Table 3, FIG. 6). The structure of domain I consists of an anti-parallel β-sheet with four short strands and four α-helices. The β-sheet of domain I contains the C-terminal end of the strand 11 (β4 in aerolysin convention), the longest in the molecule, a type 1' β-turn, strand 12 and a β-hair-pin between helix 2 and 3. The β-turn between strand 11 and strand 12 is shortened by two residues in the MP467 model compared with parasporin-2. Domain I contains a surface hydrophobic patch consisting of Phe26, Val48, Pro50, Ile52, Tyr56, Met193, Val202, His205, Tyr206, Phe207, Trp208, Phe209, and Leu210 (motif shown in SEQ ID NO: 13). The hydrophobic patch is approximately 198 Å$^2$ (17.7 Å×11.2 Å) encompassing strand 12, helix 2, helix 3 and the type 1' β-turn between strand 11 and strand 12. (FIG. 6) Literature evidence strongly suggests that Domain I of the aerolysin-type beta-pore-forming-toxins (β-PFTs) is involved in receptor binding. (Abe, 2008) (Tateno, 2003) (Lafont, 2004) (Song, 1996) (Olson, 1999)

Domain II and III adopt a highly twisted topology made of almost entirely β strands and defines as the conserved aerolysin fold (Szczesny et al., 2011). Domain II is a five-stranded anti-parallel β-sheet (β5/6-β11-β13-β7-β10, where both β5 and 6 can be viewed as a broken one long strand) patched on one side by an amphipathic β-hairpin β8 and 9 (FIG. 6). This hairpin stemmed from β7 and β10 forms a hydrophobic core with the central β-sheet, but it is too thin to cover the whole inner surface. This has forced the edge of central sheet to curl toward the hairpin and to wrap the uncovered surface. In enterotoxin CPE (3am2), the corresponding β-hairpin undergoes a drastic conformational change and assumes an α-helix, but its amphipathic characteristic essential for structural stability is well preserved. The same five β-strands of domain 2 extend and refold into domain 3 with a beta-sandwich structure. Three strands β5/6-β11-β13 make a 180° twist in middle forming a new 3 stranded β-sheet as one side of β-sandwich. The β7 and β10 spray from the central sheet, also twist in middle, and hydrophobically pack against strands β5/6-β11-β13. These natural β-sheet twisting points provide a convenient domain divider. The β5/6 usually does not hold the β conformation along its whole length due to twist and separates into two linked β strands as β5 and β6. Apparently, this usual topology strikes a balance between protein structural stability and flexibility critical to conformational transition from soluble to pore forming state.

On the surface of domain II and III, there is a stripe of solvent exposed serine and threonine residues (FIG. 4). β-strand 10 contains 3 serine and 4 threonine residues with average solvent accessibility of 78.5 Å$^2$. These residues occur in an "every-other-one" motif from N to C-terminus of the β-strand 10. β-strand 7 also contains a stretch of 3 serine and 2 threonine residues with average solvent exposure of 59.3 Å$^2$. This distinct serine/threonine stripe has been observed in the aerolysin-type beta-pore-forming-toxins (β-PFTs). (Rossjohn, 1998) It has been proposed that this feature may be involved in aligning the molecule parallel to membrane after initial receptor binding by domain I. (Akiba, 2009)

Based on structural comparison and biochemistry essay, various aerolysin-like toxins despite their distinct target specificity are thought to share the same mode of action, β-barrel pore formation in membrane. The toxin is produced as a soluble protein which diffuses towards its target cell where it binds via specific surface receptors. Once receptor bound, the toxin undergoes circular polymerization, generating ring like structures that subsequently insert into the membrane and form a pore. While aerolysin and e-toxin form heptamers, the stochiometry might differ between members. Multiple lines of evidences back up a notation that the pore forming is carried out with the conserved beta hairpin. First, the β-barrel conformation across membrane positions residues along the pore wall facing either hydrophobic lipid bilayer or hydrophilic pore lumen. Thus, the sequence of the transmembrane insertion elements must at least have the alternating pattern of polar and hydrophobic residues although any distinct sequence conservation might be not strictly required. The sequence alignment among the inserting β-hairpin from the typical aerolysin-like toxins including MP467 demonstrated that this amphipathic pattern is largely persevered (FIG. 3). In fact, the hairpin is one of most conserved elements on the whole sequence. Second, the crystal structure of heptameric pore of *Staphylococcus aureus* α-hemolysin presented a membrane β pore confirmation, and clearly showed that the pore stem is made of amphipathic β-hairpins (Song et al., 1996). Despite the sequence difference from areolysins, the hairpin alternating pattern is also observed (FIG. 3). Third, it has been experimentally demonstrated that a similar amphipathic β-hairpin is the pore-forming element in *Clostridium septicum* alpha toxin (Melton et al., 2009), a sequence homolog of aerolysin and mp467s. Using deletion mutagenesis, cysteine-scanning mutagenesis and multiple spectrofluorimetric methods, the applicants showed that either removing the hairpin by deletion or restricting its movement by engineered disulfide abolishes alpha toxin's pore forming capability but does not affect other functions.

TABLE 3

Domain residues of MP467 (SEQ ID NO: 2)

| Domain | Start | End |
|---|---|---|
| I | 1 | 65 |
|  | 187 | 223 |
| II | 66 | 79 |
|  | 104 | 154 |
|  | 175 | 186 |
|  | 224 | 234 |
| III | 80 | 103 |
|  | 155 | 174 |
|  | 235 | 246 |

We conclude that the constellation of hydrophobic residues within the hydrophobic patch and the conformation of the type 1' β-turn in domain I and the arrangement of serine/threonine residues throughout domain II and III are in part responsible for the insecticidal activity of MP467. Through our sequence and structural comparisons we predict the PS2 (Cry46a) and hydrolysin proteins should have similar activity to MP467.

Example 2

*Lepidoptera* and *Coleoptera* Assays with Purified Proteins

Insecticidal activity bioassay screens were conducted to evaluate the effects of the insecticidal proteins on a variety of *Lepidoptera* species (European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*)), a *Coleoptera* specie (Western corn rootworm (*Diabrotica virgifera*)

*Lepidoptera* feeding assays were conducted on an artificial diet containing the cleared lysates of bacterial strains in a 96 well plate set up. The cleared lysate was incorporated with the *Lepidopteran*-specific artificial diet in a ratio of 20 ul cleared lysate and 40 ul of diet mixture. Two to five neonate larvas were placed in each well to feed ad libitum for 5 days. Results were expressed as positive for larvae reactions such as stunting and or mortality. Results were expressed as negative if the larvae were similar to the negative control that is feeding diet to which the above buffer only has been applied. Each cleared lysate was assayed on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*). A series of concentrations of the purified protein sample was assayed against those insects and concentrations for 50% mortality (LC50) or inhibition of 50% of the individuals (IC50) were calculated. The results are shown in Tables 4 and 5.

*Coleoptera* feeding assays were conducted on an artificial diet containing the cleared lysates of bacterial strains in a 96 well plate set up. The cleared lysate was incorporated with the coleopteran-specific artificial diet in a ratio of 10 ul cleared lysate and 50 ul of diet mixture. Two to five Western corn rootworm (*Diabrotica virgifera*) neonate larva were placed in each well to feed ad libitum for 5 days. Results were expressed as positive for larvae reactions such as stunting and or mortality. Results were expressed as negative if the larvae were similar to the negative control that is feeding diet to which the above buffer only has been applied. A series of concentrations of the purified protein sample was assayed against those insects and concentrations for 50% mortality (LC50) or inhibition of 50% of the individuals (IC50) were calculated. The results are shown in Tables 4 and 5.

TABLE 4

Insecticidal activity of MP467 (SEQ ID NO: 2)

| Insect | LC/IC | MP467, ppm | Lower 95% Confidence Limit | Upper 95% Confidence Limit |
|---|---|---|---|---|
| CEW | LC50 | 279.8 | 61.71 | 1268 |
|  | IC50 | 146.3 | 121.9 | 177.6 |
| FAW | LC50 | >320 (40% mort.) |  |  |
|  | IC50 | 295.6 | 236.3 | 443.3 |
| BCW | LC50 | 204.8 | 173.4 | 244.2 |
|  | IC50 | 111.9 | 96.28 | 130.7 |
| SBL | LC50 | 212.5 | 177 | 252.3 |
|  | IC50 | 120.18 | 99.5 | 142.4 |
| VBC | LC50 | 54.72 | 41.25 | 67.1 |
|  | IC50 | 43.49 | 32.42 | 53.3 |
| *Coleopteran* | | | | |
| WCRW | LC50 | 65.84 | 56.07 | 76 |
|  | IC50 | 25.96 | 22.94 | 29.61 |
| *Lygus* | LC50 | 22.2 | 19.6 | 25.2 |

TABLE 5

Insecticidal activity of Cry46Aa (SEQ ID NO: 10)

| Insect | ILC50, ppm |
|---|---|
| WCRW | 32 |
| *Lygus* | 69 |
| ECB | >230 |
| BCW | 32 |
| CEW | 195 |
| FAW | >230 |
| SBL | 36 |

Example 3

*Lygus*/Stinkbug Bioassay with Purified Proteins

*Lygus* (*Lygus hesperus*) bioassays were conducted using the cell lysate samples mixed with insect diet (Bio-Serv F9644B) in each well of a 96 well bioassay plate (BD Falcon™ 353910). A variable number of *Lygus hesperus* second instar nymphs (2 to 7) were placed into each well of a 96 well plate. The assay was run four days at 25° C. and then was scored for insect mortality and stunting of insect growth. A series of concentrations of the purified protein sample was assayed against those insects and concentrations for 50% mortality (LC50) or inhibition of 50% of the individuals (ILC50) were calculated.

The *lygus* assay was run with 15 $2^{nd}$ stage instars per petri dish with 3 reps per dose. Doses were 40 ul sample at 3 mg/ml MP467 or Cry46Aa+360 ul diet. The assay ran 4 days. Results are in Tables 4 and 5.

Example 4

Identification of Motifs for Insecticidal Activity: Domain I Hydrophobic Patch Mutagenesis Saturation mutagenesis was performed on residues in the hydrophobic patch of domain I, specifically Tyr206 and Trp208 as well as site directed mutagenesis at Phe207 and Phe209. These residues appear to be important in determining hemolytic and insecticidal activities of MP467. Results for Western Corn Rootworm (WCRW) are shown in Table 6.

Site directed mutagenesis was performed on the serines and threonines within strand 10 replacing them with alanine residues. Table 6 also contains the bioassay data for the β-strand10 and 7 serine/threonine to alanine mutant. These mutants lack all insecticidal activity.

In Table 6, "R" denotes a reduction in activity over the wild-type, "=" denotes the activity similar to wild-type and "-" denotes no WCRW activity.

TABLE 6

| Gene Name | AA position and change | WCWR Bioassay Data |
|---|---|---|
| MP467-M1 | W208A | R |
| MP467-M2 | D204A | = |
| MP467-M3 | H205A | R |
| MP467-M4 | Y206A | R |
| MP467-M5 | F207A | R |
| MP467-M6 | F209A | R |
| MP467-M7 | Y56A | R |
| MP467-M8 | H58A | R |
| MP467-M9 | W208R | R |
| MP467-M10 | W208N | R |
| MP467-M11 | W208D | R |
| MP467-M12 | W208C | R |
| MP467-M13 | W208Q | = |
| MP467-M14 | W208E | = |
| MP467-M15 | W208G | - |
| MP467-M16 | W208H | = |
| MP467-M17 | W208I | = |
| MP467-M18 | W208L | = |
| MP467-M19 | W208K | R |
| MP467-M20 | W208M | = |
| MP467-M21 | W208F | = |
| MP467-M22 | W208P | - |
| MP467-M23 | W208S | = |
| MP467-M24 | W208T | = |
| MP467-M25 | W208Y | = |
| MP467-M26 | W208V | = |
| MP467-M40 | Y206R, W208M | - |
| MP467-M41 | Y206N, W208M | R |
| MP467-M42 | Y206D, W208M | - |
| MP467-M43 | Y206C, W208M | - |
| MP467-M44 | Y206Q, W208M | - |
| MP467-M45 | Y206E, W208M | - |
| MP467-M46 | Y206G, W208M | - |
| MP467-M47 | Y206H, W208M | - |
| MP467-M48 | Y206I, W208M | - |
| MP467-M49 | Y206L, W208M | - |
| MP467-M50 | Y206K, W208M | - |
| MP467-M51 | Y206M, W208M | - |
| MP467-M52 | Y206F, W208M | = |
| MP467-M53 | Y206S, W208M | - |
| MP467-M54 | Y206T, W208M | - |
| MP467-M55 | Y206W, W208M | R |
| MP467-M56 | Y206V, W208M | - |

TABLE 6-continued

| Gene Name | AA position and change | WCWR Bioassay Data |
|---|---|---|
| MP467-M57 | Y206R | R |
| MP467-M58 | Y206N | = |
| MP467-M59 | Y206D | R |
| MP467-M60 | Y206C | - |
| MP467-M61 | Y206Q | R |
| MP467-M62 | Y206E | - |
| MP467-M63 | Y206G | - |
| MP467-M64 | Y206H | = |
| MP467-M65 | Y206I | = |
| MP467-M66 | Y206L | = |
| MP467-M67 | Y206K | - |
| MP467-M68 | Y206M | = |
| MP467-M69 | Y206F | R |
| MP467-M70 | Y206S | R |
| MP467-M71 | Y206T | R |
| MP467-M72 | Y206W | = |
| MP467-M73 | Y206V | R |

Example 5

Transient Expression and Insect Bioassay on Transient Leaf Tissues

MP467 was cloned into a transient expression vector under control of the maize ubiquitin promoter (Christensen and Quail, (1996) *Transgenic Research* 5:213-218) and a duplicated version of the promoter from the mirabilis mosaic virus (DMMV PRO; Dey and Maiti, (1999) *Plant Mol. Biol.,* 40:771-82). The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122: 101-108). Briefly, young plantlets of maize were agro-infiltrated with normalized bacterial cell cultures of test and control strains. Leaf discs were generated from each plantlet and infested WCRW (*Diabrotica virgifera*) along with appropriate controls. The degree of consumption of green leaf tissues was scored after 2 days of infestation. Transient protein MP467 protein was used as a standard.

After 2d feeding, the amount of leaf tissue consumed by WCRW larvae was scored across 24 disks per treatment. When compare to negative control (DsRed), tissue accumulating MP467 was significantly less damaged across the 24 disks. A particular promoter/gene design combination (DMMV PRO:MP467 (MODA), provided as much protection as a known positive control.

Example 6

Transformation of Maize by Particle Bombardment and Regeneration of Transgenic Plants Immature maize embryos from greenhouse donor plants are bombarded with a DNA molecule containing the toxin nucleotide sequence (e.g., SEQ ID NOs: 1 or 9) operably linked to a suitable promoter and a suitable selectable marker gene (e.g. PAT, Wohlleben, et al., (1988) *Gene* 70: 25-37; which confers resistance to the herbicide Bialaphos). Alternatively, the selectable marker gene is provided on a separate DNA molecule. Transformation is performed as follows. Media recipes follow below.

Preparation of Target Tissue

The ears are husked and surface sterilized in 30% CLOROX™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

Preparation of DNA

A plasmid vector comprising a nucleotide sequence (e.g., SEQ ID NO: 1) operably linked to an ubiquitin promoter is made. For example, a suitable transformation vector comprises a UBI1 promoter from *Zea mays*, a 5' UTR from UBI1 and a UBI1 intron, in combination with a PinII terminator. The vector additionally contains a PAT selectable marker gene driven by a CAMV35S promoter and includes a CAMV35S terminator. Optionally, the selectable marker can reside on a separate plasmid. A DNA molecule comprising a toxin nucleotide sequence as well as a PAT selectable marker is precipitated onto 1.1 μm (average diameter) tungsten pellets using a $CaCl_2$ precipitation procedure as follows:

100 μL prepared tungsten particles in water
10 μL (1 μg) DNA in Tris EDTA buffer (1 μg total DNA)
100 μL 2.5 M $CaCl_2$
10 μL 0.1 M spermidine Each reagent is added sequentially to a tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the toxin by assays known in the art or as described above.

Bombardment and Culture Media

Bombardment medium (560Y) comprises 4.0 g/L N6 basal salts (SIGMA C-1416), 1.0 mL/L Eriksson's Vitamin Mix (1000×SIGMA-1511), 0.5 mg/L thiamine HCl, 120.0 g/L sucrose, 1.0 mg/L 2,4-D and 2.88 g/L L-proline (brought to volume with deionized $H_2O$ following adjustment to pH 5.8 with KOH); 2.0 g/L Gelrite™ (added after bringing to volume with dl H$_2$0); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with dl H$_2$0 following adjustment to pH 5.8 with KOH); 3.0 g/L Gelrite™ (added after bringing to volume with dl H$_2$0); and 0.85 mg/L silver nitrate and 3.0 mg/L Bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCl, 0.10 g/L pyridoxine HCl, and 0.40 g/L Glycine brought to volume with polished D-I H$_2$0) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished dl H$_2$0 after adjusting to pH 5.6); 3.0 g/L Gelrite™ (added after bringing to volume with dl H$_2$0); and 1.0 mg/L indoleacetic acid and 3.0 mg/L Bialaphos (added after sterilizing the medium and cooling to 60° C.).

Hormone-free medium (272V) comprises 4.3 g/L MS salts (GIBCO 11117-074), 5.0 mL/L MS vitamins stock solution (0.100 g/L nicotinic acid, 0.02 g/L thiamine HCl, 0.10 g/L pyridoxine HCl, and 0.40 g/L Glycine brought to volume with polished dl H$_2$0), 0.1 g/L myo-inositol, and 40.0 g/L sucrose (brought to volume with polished dl H$_2$0 after adjusting pH to 5.6); and 6 g/L Bacto-agar (added after bringing to volume with polished dl H$_2$0), sterilized and cooled to 60° C.

Example 7

*Agrobacterium*-Mediated Transformation of Maize and Regeneration of Transgenic Plants For *Agrobacterium*-mediated transformation of maize with a toxin nucleotide sequence (e.g., SEQ ID NO: 1 or 9), the method of Zhao can be used (U.S. Pat. No. 5,981,840 and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the toxin nucleotide sequence (SEQ ID NO: 1) to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 8

Transformation of Soybean Embryos

Soybean embryos are bombarded with a plasmid containing the toxin nucleotide sequence of SEQ ID NO: 1 operably linked to a suitable promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation includes, but is not limited to: the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188), and the 3' region of the nopaline synthase gene from the T-DNA of the Ti plasmid of *Agrobacterium tumefaciens*. The expression cassette comprising a toxin nucleotide sequence (e.g., SEQ ID NO: 1) operably linked to a suitable promoter can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, certain changes and modifications may be practiced within the scope of the appended claims.

REFERENCES CITED

Abe, Y. S. (2008). Raft-targeting and oligmerization of parasporin-2, a *Bacillus Thuringiensis* crystal protein with anti-tumour activity. *J. Biochem.* 143, 269-275.

Akiba, T., Kitada S, Kusaka Y, Ito A, et al. (2009). Crystal Structure of the Parasporin-2 *Bacillus thuringiensis* Toxin That Recognizes Cancer Cells. *J. Mol. Biol.*, 121-133.

Lafont, F. A. (2004). Bacterial subversion of lipid rafts. *Curr. Opin. Microbiol.* 7, 4-10.

Olson, R. N. (1999). Crystal structure of staphylococcal LukF delineates conformational changes accompanying formation of a transmembrane channel. *Nat. Struct. Biol.* 6, 134-140.

Rossjohn, J. F. (1998). Aerolysin-a paradigm for membrane insertion of beta-sheet protein toxins? *J. Struct. Biol* 121, 92-100.

Song, L. H. (1996). Structure of staphylococcal a-heomlysin, a heptameric transmembrane pore. *Science* 274, 1859-1866.

Tateno, H. G. (2003). Molecular cloning, expression and characterization of novel hemolytic lectins from mushroom *Laetiporus sulphureus* which show homolgy to bacterial toxins. *J. Biol. Chem.* 278, 40455-40463.

Mancheño J M, Tateno H, Goldstein I J, Martinez-Ripon M, Hermoso J A (2005) Structural analysis of the *Laetiporus sulphureus* hemolytic pore-forming lectin in complex with sugars. *J Biol Chem* 280: 17251-17259.

Akiba T, Abe Y, Kitada S, Kusaka Y, Ito A, et al. (2009) Crystal structure of the parasporin-2 *Bacillus thuringiensis* toxin that recognizes cancer cells. *J Mol Biol* 386: 121-133.

Cole A R, Gibed M, Popoff M, Moss D S, Titball R W, et al. (2004) *Clostridium perfringens* epsilon-toxin shows structural similarity to the pore-forming toxin aerolysin. *Nat Struct Mol Biol* 11: 797-798.

Melton J A, Parker M W, Rossjohn J, Buckley J T and Tweten R K (2004). The identification and structure of the membrane-spanning domain of the *clostridium septicum* alpha toxin. *The Journal of Biological Chemistry.* 279(14): 14315-14322.

Szczesny et al., 2011 P. Szczesny, I. lacovache, A. Muszewska, K. Ginalski, F. G. van der Goot, M. Grynberg Extending the aerolysin family: from bacteria to vertebrates, *PLoS ONE*, 6 (2011), p. e20349.

J. Rossjohn, S. C. Feil, W. J. McKinstry, D. Tsernoglou, G. van der Goot, J. T. Buckley, M. W. Parker Aerolysin—a paradigm for membrane insertion of beta-sheet protein toxins? J. Struct. Biol., 121 (1998), pp. 92-100.

Kitadokoro K, Nishimura K, Kamitani S, Fukui-Miyazaki A, Toshima H, Abe H, Kamata Y, Sugita-Konishi Y, Yamamoto S, Karatani H, Horiguchi Y. Crystal structure of *Clostridium perfringens* enterotoxin displays features of beta-pore-forming toxins. *J Biol Chem.* 2011 Jun. 3; 286(22):19549-55.

That which is claimed:

1. An isolated nucleic acid molecule selected from the group consisting of:
   (a) a nucleic acid molecule comprising the nucleotide sequence of SEC ID NO: 1;
   (b) a nucleic acid molecule which encodes a polypeptide comprising the amino acid sequence of SEC ID NO: 2;
   (c) a nucleic acid molecule encoding a protein having insecticidal activity comprising an amino acid sequence having at least 95% sequence identity to the amino acid sequence of SEQ ID NO: 2; and wherein the nucleic acid molecule is operably linked to a heterologous regulatory element.

2. The isolated nucleic acid molecule of claim 1, wherein said nucleic acid molecule is a synthetic molecule that has been designed for expression in a plant.

3. A DNA construct comprising the nucleic acid molecule of claim 1.

4. The DNA construct of claim 3, further comprising a nucleic acid molecule encoding a heterologous polypeptide.

5. A host cell that contains the DNA construct of claim 3.

6. The host cell of claim 5 that is a bacterial cell.

7. The host cell of claim 5 that is a plant cell.

8. A transgenic plant comprising the host cell of claim 7.

9. The transgenic plant of claim 8, wherein said plant is selected from the group consisting of maize, sorghum, wheat, cabbage, sunflower, tomato, crucifers, peppers, potato, cotton, rice, soybean, sugar beet, sugarcane, tobacco, barley, and oilseed rape.

10. Transformed seed of the plant of claim 9, wherein the seed comprise the DNA construct.

11. A plant having stably incorporated into its genome a DNA construct comprising:
    a nucleotide sequence that encodes a protein having insecticidal activity, wherein said nucleotide sequence is selected from the group consisting of:
    (a) a nucleic acid molecule comprising the nucleotide sequence of SEQ ID NO: 1;
    (b) a nucleic acid molecule which encodes a polypeptide comprising the amino acid sequence of SEQ ID NO: 2; and
    (c) a nucleotide sequence encoding a protein having insecticidal activity comprising an amino acid sequence having at least 95% sequence identity to the amino acid sequence of SEQ ID NO:2; and a heterologous promoter, wherein said nucleotide sequence is operably linked to the heterologous promoter that drives expression of the nucleotide sequence in a plant cell.

\* \* \* \* \*

SEQUENCE LISTING

```
<160> NUMBER OF SEQ ID NOS: 22

<210> SEQ ID NO 1
<211> LENGTH: 777
<212> TYPE: DNA
<213> ORGANISM: Bacillus sphaericus
<220> FEATURE:
<221> NAME/KEY: misc_feature
<222> LOCATION: (1)..(777)
<223> OTHER INFORMATION: MP467S nucleotide sequence

<400> SEQUENCE: 1
atgacaattc aagaaaaatt atcatttaca gatttacctg cactaaaatc aagccccgag      60
agtgtaagac aagcattcac aaataagttt ggtacaaaac ctgatggcat ctctgtcaac     120
agtgaaactt attttaatgc tgtcaaacct gcaatcacag aacaatatgg acaccttgt      180 tataaaagac taggtgactt taattatatg aaaggcgatg gcaagccacc tacatctgca     240
atcgttggga gcaatgtagc agtaaactat ggagatgaag aggctacgat gactttagag     300
gttcaaggaa gctggcaaag tgagcaatct tggtcttctg aaagtacgac tggtctaacg     360
atatcctcca aatttacaat tgaaggattc tttgaatcag gaatggagtt ttctgtcagt     420
actactgttg gggaaacaaa aactgagtca gaatcaagaa cagccactgc cagtgtacaa     480
```

```
gtgactgtgc cgcctagaag taaaaaacaa gtaacaatgg ttggtacatt gaaaaaagaa        540
tccatgaact tccgagcacc tatttcagtt gatggcatgt ttggggcaaa cttccctaaa        600
cgagtacaag accattattt ctggttcctt ggtgcaggta gtgtattgac tcaaacaaca        660
ggagaaatca ctggtactat taaaaataca gctgtctttg atgttcatac ggaaattggc        720
aaaacagaac cattaactgc agaagagcta agcaaacttg ctgtattagc taagtaa          777
```

```
<210> SEQ ID NO 2
<211> LENGTH: 258
<212> TYPE: PRT
<213> ORGANISM: Bacillus sphaericus
<220> FEATURE:
<221> NAME/KEY: MISC_FEATURE
<222> LOCATION: (1)..(258)
<223> OTHER INFORMATION: MP467S

<400> SEQUENCE: 2
```

Met Thr Ile Gln Glu Lys Leu Ser Phe Thr Asp Leu Pro Ala Leu Lys
1               5                   10                  15

Ser Ser Pro Glu Ser Val Arg Gln Ala Phe Thr Asn Lys Phe Gly Thr
            20                  25                  30

Lys Pro Asp Gly Ile Ser Val Asn Ser Glu Thr Tyr Phe Asn Ala Val
        35                  40                  45

Lys Pro Ala Ile Thr Glu Gln Tyr Gly His Pro Cys Tyr Lys Arg Leu
    50                  55                  60

Gly Asp Phe Asn Tyr Met Lys Gly Asp Gly Lys Pro Pro Thr Ser Ala
65                  70                  75                  80

Ile Val Gly Ser Asn Val Ala Val Asn Tyr Gly Asp Glu Glu Ala Thr
                85                  90                  95

Met Thr Leu Glu Val Gln Gly Ser Trp Gln Ser Glu Gln Ser Trp Ser
            100                 105                 110

Ser Glu Ser Thr Thr Gly Leu Thr Ile Ser Ser Lys Phe Thr Ile Glu
        115                 120                 125

Gly Phe Phe Glu Ser Gly Met Glu Phe Ser Val Ser Thr Thr Val Gly
    130                 135                 140

Glu Thr Lys Thr Glu Ser Glu Ser Arg Thr Ala Thr Ala Ser Val Gln
145                 150                 155                 160

Val Thr Val Pro Pro Arg Ser Lys Lys Gln Val Thr Met Val Gly Thr
                165                 170                 175

Leu Lys Lys Glu Ser Met Asn Phe Arg Ala Pro Ile Ser Val Asp Gly
            180                 185                 190

Met Phe Gly Ala Asn Phe Pro Lys Arg Val Gln Asp His Tyr Phe Trp
        195                 200                 205

Phe Leu Gly Ala Gly Ser Val Leu Thr Gln Thr Gly Glu Ile Thr
    210                 215                 220

Gly Thr Ile Lys Asn Thr Ala Val Phe Asp Val His Thr Glu Ile Gly
225                 230                 235                 240

Lys Thr Glu Pro Leu Thr Ala Glu Glu Leu Ser Lys Leu Ala Val Leu
                245                 250                 255

Ala Lys

```
<210> SEQ ID NO 3
<211> LENGTH: 735
<212> TYPE: DNA
<213> ORGANISM: Hydra vulgaris
<220> FEATURE:
```

```
<221> NAME/KEY: misc_feature
<222> LOCATION: (1)..(735)
<223> OTHER INFORMATION: hydralysin-2 nucleotide sequence

<400> SEQUENCE: 3
atgggtaaag agcttctaac ctttagtgat ctaacatggc tggacagtag tccagacact    60
gttcgaagtg cttttacgag acagtatggg acaacgcctg atggcattgc tctaaacagt   120
gaaggttact ttggttacca cagtccgcca atcactgaac agtatggccg tccatgctac   180
aaacagactg gcgaaacaaa aattacgttg caagacttag ctcctcctac ggatgctatt   240
ctcggaaact ctattgccag aaatcgaggt gactcgccga ttactttgac cgtaagcgtt   300
gaaggcaaat ggagcgattc tacaagctgg tcaacaagca cagaaacagg agtaaaaatg   360
tcaagtgagt ttggagttga aggagctttc aaaatgggag gagaattttc acttacggta   420
tcagtaggaa agtctggttc cagcagtgtg gaaaagactt caacttcatc tgttcaagta   480
actgttcctc cgcgttcgaa ggttgttgtt agcatggttg gtattatgaa aaaggaaaag   540
gtattcttcg aggttccagt caccgttgat ggaagtttcg gtgctaactt cccttcaaca   600
gttcaaggtc actactttg gtttatggac gctcgcagtt gtctaaataa aacgtctggt   660
gtcatcaaag gtacgattga ccacgccaac gtgtttgacg tttcggttga agtcggacca   720
agtgagcctt gtaa                                                      735

<210> SEQ ID NO 4
<211> LENGTH: 244
<212> TYPE: PRT
<213> ORGANISM: Hydra viridissima
<220> FEATURE:
<221> NAME/KEY: MISC_FEATURE
<222> LOCATION: (1)..(244)
<223> OTHER INFORMATION: hydralysin-2

<400> SEQUENCE: 4

Met Gly Lys Glu Leu Leu Thr Phe Ser Asp Leu Thr Trp Leu Asp Ser
1               5                   10                  15

Ser Pro Asp Thr Val Arg Ser Ala Phe Thr Arg Gln Tyr Gly Thr Thr
            20                  25                  30

Pro Asp Gly Ile Ala Leu Asn Ser Glu Gly Tyr Phe Gly Tyr His Ser
        35                  40                  45

Pro Pro Ile Thr Glu Gln Tyr Gly Arg Pro Cys Tyr Lys Gln Thr Gly
    50                  55                  60

Glu Thr Lys Ile Thr Leu Gln Asp Leu Ala Pro Pro Thr Asp Ala Ile
65                  70                  75                  80

Leu Gly Asn Ser Ile Ala Arg Asn Arg Gly Asp Ser Pro Ile Thr Leu
                85                  90                  95

Thr Val Ser Val Glu Gly Lys Trp Ser Asp Ser Thr Ser Trp Ser Thr
            100                 105                 110

Ser Thr Glu Thr Gly Val Lys Met Ser Ser Glu Phe Gly Val Glu Gly
        115                 120                 125

Ala Phe Lys Met Gly Gly Glu Phe Ser Leu Thr Val Ser Val Gly Lys
    130                 135                 140

Ser Gly Ser Ser Ser Val Glu Lys Thr Ser Thr Ser Ser Val Gln Val
145                 150                 155                 160

Thr Val Pro Pro Arg Ser Lys Val Val Val Ser Met Val Gly Ile Met
                165                 170                 175

Lys Lys Glu Lys Val Phe Phe Glu Val Pro Val Thr Val Asp Gly Ser
            180                 185                 190
```

```
Phe Gly Ala Asn Phe Pro Ser Thr Val Gln Gly His Tyr Phe Trp Phe
        195                 200                 205

Met Asp Ala Arg Ser Cys Leu Asn Lys Thr Ser Gly Val Ile Lys Gly
    210                 215                 220

Thr Ile Asp His Ala Asn Val Phe Asp Val Ser Val Glu Val Gly Pro
225                 230                 235                 240

Ser Glu Pro Leu

<210> SEQ ID NO 5
<211> LENGTH: 762
<212> TYPE: DNA
<213> ORGANISM: Bacillus thuringiensis
<220> FEATURE:
<221> NAME/KEY: misc_feature
<222> LOCATION: (1)..(762)
<223> OTHER INFORMATION: 543S nucleotide sequence

<400> SEQUENCE: 5
atgattatac aagaaaaatt atctttttca gatctagatt cattagattc aactacagac      60
tccataatgg atgcgtttaa agatctttat ggaatacttc ctgacgaaat tgcattaaat     120
aatgagacgt ttccaattca taataagcct gctattactg aacgttatgg tcatgcttgt     180
tataaaatgc tgggcccttt tatatttcga tatcttgaag aaccttcaat aaatgaaata     240
accctaaagg aacaatttgt atataatcct aataatgaag aaaaagagat tgtagtgaca     300
ataaaagaac aatgggtcaa tatacaatct tggagttcga aatctattac aggtttaact     360
ttaaaatcag atcttattat tgcaggtaaa tttcaatcgg gtaatgaatt taatatttca     420
acttttgtag gagaaagtaa ttcaaaatca attcatacct ctccttcaat tgaacattct     480
attaaagtac ctccaaatag taaaatgaaa attgcaatga taggaacatt aattactgag     540
gttctacatt tccaatcaat tataacagta caaggcatgt ttggtgcatg ttttccacgt     600
atggttcgtg gacattatat tgggtttaaa agcgccggtc acatcctaaa taaaacgttt     660
ggaataattg aaggatctat taacaataca gcaattcagg atattgaaat aaatattaaa     720
gggatagaac cttattccta taaacaaaaa gtgatcaagt ag                        762

<210> SEQ ID NO 6
<211> LENGTH: 253
<212> TYPE: PRT
<213> ORGANISM: Bacillus thuringiensis
<220> FEATURE:
<221> NAME/KEY: MISC_FEATURE
<222> LOCATION: (1)..(253)
<223> OTHER INFORMATION: 543S

<400> SEQUENCE: 6

Met Ile Ile Gln Glu Lys Leu Ser Phe Ser Asp Leu Asp Ser Leu Asp
1               5                   10                  15

Ser Thr Thr Asp Ser Ile Met Asp Ala Phe Lys Asp Leu Tyr Gly Ile
            20                  25                  30

Leu Pro Asp Glu Ile Ala Leu Asn Asn Glu Thr Phe Pro Ile His Asn
        35                  40                  45

Lys Pro Ala Ile Thr Glu Arg Tyr Gly His Ala Cys Tyr Lys Met Leu
    50                  55                  60

Gly Pro Phe Ile Phe Arg Tyr Leu Glu Glu Pro Ser Ile Asn Glu Ile
65                  70                  75                  80

Thr Leu Lys Glu Gln Phe Val Tyr Asn Pro Asn Asn Glu Glu Lys Glu
                85                  90                  95
```

Ile Val Val Thr Ile Lys Glu Gln Trp Val Asn Ile Gln Ser Trp Ser
              100                 105                 110

Ser Lys Ser Ile Thr Gly Leu Thr Leu Lys Ser Asp Leu Ile Ile Ala
          115                 120                 125

Gly Lys Phe Gln Ser Gly Asn Glu Phe Asn Ile Ser Thr Phe Val Gly
      130                 135                 140

Glu Ser Asn Ser Lys Ser Ile His Thr Ser Pro Ser Ile Glu His Ser
145                 150                 155                 160

Ile Lys Val Pro Pro Asn Ser Lys Met Lys Ile Ala Met Ile Gly Thr
                165                 170                 175

Leu Ile Thr Glu Val Leu His Phe Gln Ser Ile Ile Thr Val Gln Gly
              180                 185                 190

Met Phe Gly Ala Cys Phe Pro Arg Met Val Arg Gly His Tyr Ile Gly
          195                 200                 205

Phe Lys Ser Ala Gly His Ile Leu Asn Lys Thr Phe Gly Ile Ile Glu
      210                 215                 220

Gly Ser Ile Asn Asn Thr Ala Ile Gln Asp Ile Glu Ile Asn Ile Lys
225                 230                 235                 240

Gly Ile Glu Pro Tyr Ser Tyr Lys Gln Lys Val Ile Lys
                245                 250

<210> SEQ ID NO 7
<211> LENGTH: 762
<212> TYPE: DNA
<213> ORGANISM: Bacillus thuringiensis
<220> FEATURE:
<221> NAME/KEY: misc_feature
<222> LOCATION: (1)..(762)
<223> OTHER INFORMATION: 544s nucleotide sequence

<400> SEQUENCE: 7
atgattatac aagaaaaatt atcttttca gatttagatt cattaggttc aactacagat      60
tccataatgg acgcgtttaa agatctttat gggctacttc cttatgaaat cgcaataaat     120
aatgagacat ttccaattca taataagcct gctattactg aacgttatgg tcacgcttgt    180
tataaaacgc ttggcccttt tatattcagc aatattgaag agccttcaaa gaatgaagta    240
agcctagggg aacaatttgt atttaatcct agtaatgaag aagcagaaat tatagtcaca    300
ataaaagagc aatgggctaa tattcaatct ggacttcgg aatctactac aggtttaact    360
ttaacatcag attttacgat ggaaggtgaa tttcaattcg gcaacaaatt taatatttca    420
actttggtgg agaaagtaa ttcaaaatcc atcattacct cccttccat tgagcgttct     480
attaaagtac ctccaaatag taagataaaa gttactacag tcggaacatt aattacagaa    540
attctacatt tccaatcaat tatatcggta acggtatgt ttggtgcatg ttttccacgg     600
atggttcgtg gcattacgt tggattcaaa agtgccggtc acatcctaaa taaacattt      660
ggttccatta agggggccat taatagtaca ataattaagg atattcaaat aaaaactgga    720
aagatagagc cttattttat taaccaaaaa tgggaaagtt ga                        762

<210> SEQ ID NO 8
<211> LENGTH: 253
<212> TYPE: PRT
<213> ORGANISM: Bacillus thuringiensis
<220> FEATURE:
<221> NAME/KEY: MISC_FEATURE
<222> LOCATION: (1)..(253)
<223> OTHER INFORMATION: 544s -continued

<400> SEQUENCE: 8

Met Ile Ile Gln Glu Lys Leu Ser Phe Ser Asp Leu Asp Ser Leu Gly
1 5 10 15

Ser Thr Thr Asp Ser Ile Met Asp Ala Phe Lys Asp Leu Tyr Gly Leu
20 25 30

Leu Pro Tyr Glu Ile Ala Ile Asn Asn Glu Thr Phe Pro Ile His Asn
35 40 45

Lys Pro Ala Ile Thr Glu Arg Tyr Gly His Ala Cys Tyr Lys Thr Leu
50 55 60

Gly Pro Phe Ile Phe Ser Asn Ile Glu Glu Pro Ser Lys Asn Glu Val
65 70 75 80

Ser Leu Gly Glu Gln Phe Val Phe Asn Pro Ser Asn Glu Glu Ala Glu
85 90 95

Ile Ile Val Thr Ile Lys Glu Gln Trp Ala Asn Ile Gln Ser Trp Thr
100 105 110

Ser Glu Ser Thr Thr Gly Leu Thr Leu Thr Ser Asp Phe Thr Met Glu
115 120 125

Gly Glu Phe Gln Phe Gly Asn Lys Phe Asn Ile Ser Thr Phe Val Gly
130 135 140

Glu Ser Asn Ser Lys Ser Ile Ile Thr Ser Leu Ser Ile Glu Arg Ser
145 150 155 160

Ile Lys Val Pro Pro Asn Ser Lys Ile Lys Val Thr Thr Val Gly Thr
165 170 175

Leu Ile Thr Glu Ile Leu His Phe Gln Ser Ile Ile Ser Val Asn Gly
180 185 190

Met Phe Gly Ala Cys Phe Pro Arg Met Val Arg Gly His Tyr Val Gly
195 200 205

Phe Lys Ser Ala Gly His Ile Leu Asn Lys Thr Phe Gly Ser Ile Lys
210 215 220

Gly Ala Ile Asn Ser Thr Ile Ile Lys Asp Ile Gln Ile Lys Thr Gly
225 230 235 240

Lys Ile Glu Pro Tyr Phe Ile Asn Gln Lys Trp Glu Ser
245 250

<210> SEQ ID NO 9
<211> LENGTH: 1016
<212> TYPE: DNA
<213> ORGANISM: Bacillus thuringiensis
<220> FEATURE:
<221> NAME/KEY: misc_feature
<222> LOCATION: (1)..(1016)
<223> OTHER INFORMATION: Cry46Aa nucleotide sequence

<400> SEQUENCE: 9
atgtataatg ataaaagaat gtgttctgat ccttatcagg gtatgaataa acctcattat 60
tgcaattgtc atacgtataa taatagtgaa ataaccggag ggcttcaagt agatctagat 120
aatcaagtag tggaaacatt tcaatccact acagacgtta ttcgagaata tcttatgttt 180
aatgagttat cagcattaag ttcaagtcca gaaagtgtaa gatctagatt ttcctctatt 240
tatggtacta atcccgatgg tattgcatta aataatgaaa cgtattttaa cgccgtaaaa 300
ccgcctatta ctgctcaata tggatactat tgctataaaa atgttgggac tgttcagtac 360
gtaaatagac ctactgatat taacccaaac gttattcttg ctcaagacac attaacaaat 420
aatactaatg aaccatttac tacaactatc actataactg ggtcttttac caacacgtct 480
actgtgacat ctagtacaac aacaggcttt aaatttacta gtaaactatc aattaaaaaa 540

-continued

```
gtctttgaaa ttggtggaga agtttcattc tctactacaa ttggaacatc tgaaacaact    600
acagaaacaa ttactgtatc taaatccgtt acggttacgg tccagctcaa agtagaagaa    660
ctattcagtt aacagctaaa atagcaaaag aatctgcaga ctttagtgct cctattactg    720
tcgatggtta ttttggtgct aattttccca aaagagtagg gccaggtggg cattattttt    780
ggtttaaccc cgctagggat gttctaaata ctacctctgg tacacttaga ggtacagtga    840
cgaatgtatc tagttttgac ttccaaacta tagtgcaacc agcacgcagt ttactagatg    900
aacaacaaga aactttagaa tatgccatac ctggagatcc ttctgggaa caattgcagc     960 aaatggaaca aaggatgttt ttttccaaat gccaatgccc aaaatggggg aattag       1016
```

<210> SEQ ID NO 10
<211> LENGTH: 338
<212> TYPE: PRT
<213> ORGANISM: Bacillus thuringiensis
<220> FEATURE:
<221> NAME/KEY: MISC_FEATURE
<222> LOCATION: (1)..(338)
<223> OTHER INFORMATION: Cry46Aa

<400> SEQUENCE: 10

```
Met Tyr Asn Asp Lys Arg Met Cys Ser Asp Pro Tyr Gln Gly Met Asn
1               5                   10                  15

Lys Pro His Tyr Cys Asn Cys His Thr Tyr Asn Asn Ser Glu Ile Thr
            20                  25                  30

Gly Gly Leu Gln Val Asp Leu Asp Asn Gln Val Val Glu Thr Phe Gln
        35                  40                  45

Ser Thr Thr Asp Val Ile Arg Glu Tyr Leu Met Phe Asn Glu Leu Ser
    50                  55                  60

Ala Leu Ser Ser Ser Pro Glu Ser Val Arg Ser Arg Phe Ser Ser Ile
65                  70                  75                  80

Tyr Gly Thr Asn Pro Asp Gly Ile Ala Leu Asn Asn Glu Thr Tyr Phe
                85                  90                  95

Asn Ala Val Lys Pro Pro Ile Thr Ala Gln Tyr Gly Tyr Tyr Cys Tyr
            100                 105                 110

Lys Asn Val Gly Thr Val Gln Tyr Val Asn Arg Pro Thr Asp Ile Asn
        115                 120                 125

Pro Asn Val Ile Leu Ala Gln Asp Thr Leu Thr Asn Asn Thr Asn Glu
    130                 135                 140

Pro Phe Thr Thr Thr Ile Thr Ile Thr Gly Ser Phe Thr Asn Thr Ser
145                 150                 155                 160

Thr Val Thr Ser Ser Thr Thr Thr Gly Phe Lys Phe Thr Ser Lys Leu
                165                 170                 175

Ser Ile Lys Lys Val Phe Glu Ile Gly Gly Glu Val Ser Phe Ser Thr
            180                 185                 190

Thr Ile Gly Thr Ser Glu Thr Thr Thr Glu Thr Ile Thr Val Ser Lys
        195                 200                 205

Ser Val Thr Val Thr Val Pro Ala Gln Ser Arg Arg Thr Ile Gln Leu
    210                 215                 220

Thr Ala Lys Ile Ala Lys Glu Ser Ala Asp Phe Ser Ala Pro Ile Thr
225                 230                 235                 240

Val Asp Gly Tyr Phe Gly Ala Asn Phe Pro Lys Arg Val Gly Pro Gly
                245                 250                 255

Gly His Tyr Phe Trp Phe Asn Pro Ala Arg Asp Val Leu Asn Thr Thr
            260                 265                 270
```

```
Ser Gly Thr Leu Arg Gly Thr Val Thr Asn Val Ser Ser Phe Asp Phe
        275                 280                 285

Gln Thr Ile Val Gln Pro Ala Arg Ser Leu Leu Asp Glu Gln Gln Glu
    290                 295                 300

Thr Leu Glu Tyr Ala Ile Pro Gly Asp Pro Ser Gly Leu Gln Leu Gln
305                 310                 315                 320

Gln Met Glu Gln Arg Met Phe Phe Ser Lys Cys Gln Cys Pro Lys Trp
                325                 330                 335

Gly Asn

<210> SEQ ID NO 11
<211> LENGTH: 915
<212> TYPE: DNA
<213> ORGANISM: Bacillus thuringiensis
<220> FEATURE:
<221> NAME/KEY: misc_feature
<222> LOCATION: (1)..(915)
<223> OTHER INFORMATION: Cry46Ab nucleotide sequence

<400> SEQUENCE: 11
atgtattata ctacccaagt aacaggtgga tttcaagctg atttgaataa tcaagtagtg      60
gaaacatttc aaccaagtac aaatgttatt caagaatacc ttacgtttaa tgacttacca     120
gcattaggtt caagtccaca agtgtacgc tctagatttt catctattta tggtaccaat      180
ccagatggta ttgcattaaa taatgaaaca tattttagcg ctgtacaacc accaattact     240
gttcaatatg gacactattg ttataaaaat gttgggactg ttcagtacgt aaatagaccc     300
actgatatta acccaaacgt tattctcgct caagacacat taacaaacaa tactaatgag    360
ccatttacta cgaccataac tttaacagga tcttggacca atcatccac ggttacatct     420 agtacaacaa caggtcttaa aattaccact aaactatcga ttaaaaaagt ctttgaaatt    480
ggtggagaag tttcattctc tactacaatt ggatcatctg aagcaacttc agaaacattt     540
actgtatcga aagccgtgac ggtcacagtt ccagctcaaa gtagaaggaa tattcaatta    600
acagcaaaaa tagcaagaga atctgcagat tttagtgctc ctattactgt ggatggttac    660
tttggtgcta attttcctcg tcgagtaggt ccggggggac attacttttg gtttaatcct    720
gctagagatg ttttaaatgc tacctccggt acactaagag gtaccgtgac gaatgtatct    780
agtttcgact ccaaactgt agtacaacca gcatatagtt tactggctga acagcaagaa     840
gctttagaat ctgccatatc tggagatcct tctgaggaac aattgaaaca aatacaacaa    900
acaattggat ataa                                                      915

<210> SEQ ID NO 12
<211> LENGTH: 304
<212> TYPE: PRT
<213> ORGANISM: Bacillus thuringiensis
<220> FEATURE:
<221> NAME/KEY: MISC_FEATURE
<222> LOCATION: (1)..(304)
<223> OTHER INFORMATION: Cry46Ab

<400> SEQUENCE: 12

Met Tyr Tyr Thr Thr Gln Val Thr Gly Gly Phe Gln Ala Asp Leu Asn
1               5                   10                  15

Asn Gln Val Val Glu Thr Phe Gln Pro Ser Thr Asn Val Ile Gln Glu
            20                  25                  30

Tyr Leu Thr Phe Asn Asp Leu Pro Ala Leu Gly Ser Ser Pro Gln Ser
        35                  40                  45
```

Val Arg Ser Arg Phe Ser Ser Ile Tyr Gly Thr Asn Pro Asp Gly Ile
 50                  55                  60

Ala Leu Asn Asn Glu Thr Tyr Phe Ser Ala Val Gln Pro Pro Ile Thr
 65                  70                  75                  80

Val Gln Tyr Gly His Tyr Cys Tyr Lys Asn Val Gly Thr Val Gln Tyr
                 85                  90                  95

Val Asn Arg Pro Thr Asp Ile Asn Pro Asn Val Ile Leu Ala Gln Asp
            100                 105                 110

Thr Leu Thr Asn Asn Thr Asn Glu Pro Phe Thr Thr Ile Thr Leu
        115                 120                 125

Thr Gly Ser Trp Thr Lys Ser Ser Thr Val Thr Ser Ser Thr Thr Thr
        130                 135                 140

Gly Leu Lys Ile Thr Thr Lys Leu Ser Ile Lys Lys Val Phe Glu Ile
145                 150                 155                 160

Gly Gly Glu Val Ser Phe Ser Thr Thr Ile Gly Ser Ser Glu Ala Thr
                165                 170                 175

Ser Glu Thr Phe Thr Val Ser Lys Ala Val Thr Val Thr Val Pro Ala
                180                 185                 190

Gln Ser Arg Arg Asn Ile Gln Leu Thr Ala Lys Ile Ala Arg Glu Ser
            195                 200                 205

Ala Asp Phe Ser Ala Pro Ile Thr Val Asp Gly Tyr Phe Gly Ala Asn
210                 215                 220

Phe Pro Arg Arg Val Gly Pro Gly Gly His Tyr Phe Trp Phe Asn Pro
225                 230                 235                 240

Ala Arg Asp Val Leu Asn Ala Thr Ser Gly Thr Leu Arg Gly Thr Val
                245                 250                 255

Thr Asn Val Ser Ser Phe Asp Phe Gln Thr Val Val Gln Pro Ala Tyr
            260                 265                 270

Ser Leu Leu Ala Glu Gln Gln Glu Ala Leu Glu Ser Ala Ile Ser Gly
        275                 280                 285

Asp Pro Ser Glu Glu Gln Leu Lys Gln Ile Gln Gln Thr Ile Gly Leu
        290                 295                 300

```
<210> SEQ ID NO 13
<211> LENGTH: 5
<212> TYPE: PRT
<213> ORGANISM: Artificial Sequence
<220> FEATURE:
<223> OTHER INFORMATION: hydrophobic patch motif
<220> FEATURE:
<221> NAME/KEY: MISC_FEATURE
<222> LOCATION: (1)..(5)
<223> OTHER INFORMATION: hydrophobic patch motif

<400> SEQUENCE: 13
```

His Tyr Phe Trp Phe
1                5

```
<210> SEQ ID NO 14
<211> LENGTH: 29
<212> TYPE: PRT
<213> ORGANISM: Artificial Sequence
<220> FEATURE:
<223> OTHER INFORMATION: MP467 beta hairpin region

<400> SEQUENCE: 14
```

Thr Thr Gly Leu Thr Ile Ser Ser Lys Phe Thr Ile Glu Gly Phe Phe
1               5                   10                  15

```
Glu Ser Gly Met Glu Phe Ser Val Ser Thr Thr Val Gly
            20                  25

<210> SEQ ID NO 15
<211> LENGTH: 29
<212> TYPE: PRT
<213> ORGANISM: Artificial Sequence
<220> FEATURE:
<223> OTHER INFORMATION: Parasporin-2 beta hairpin region

<400> SEQUENCE: 15

Thr Thr Gly Phe Lys Phe Thr Ser Lys Leu Ser Ile Lys Lys Val Phe
1               5                   10                  15

Glu Ile Gly Gly Glu Val Ser Phe Ser Thr Thr Ile Gly
            20                  25

<210> SEQ ID NO 16
<211> LENGTH: 29
<212> TYPE: PRT
<213> ORGANISM: Artificial Sequence
<220> FEATURE:
<223> OTHER INFORMATION: Hydralysin beta hairpin region

<400> SEQUENCE: 16

Glu Thr Gly Val Lys Met Ser Ser Glu Phe Gly Val Glu Gly Ala Phe
1               5                   10                  15

Lys Met Gly Gly Glu Phe Ser Leu Thr Val Ser Gly Val
            20                  25

<210> SEQ ID NO 17
<211> LENGTH: 29
<212> TYPE: PRT
<213> ORGANISM: Artificial Sequence
<220> FEATURE:
<223> OTHER INFORMATION: Alpha-Toxin beta hairpin region

<400> SEQUENCE: 17

Lys Ile Gly Val Lys Thr Ser Phe Lys Val Gly Leu Glu Ala Ile Ala
1               5                   10                  15

Asp Ser Lys Val Glu Thr Ser Phe Glu Phe Asn Ala Glu
            20                  25

<210> SEQ ID NO 18
<211> LENGTH: 29
<212> TYPE: PRT
<213> ORGANISM: Artificial Sequence
<220> FEATURE:
<223> OTHER INFORMATION: Aerolysin Beta hairpin region

<400> SEQUENCE: 18

Lys Val Thr Thr Lys Asn Lys Phe Lys Trp Pro Leu Val Gly Glu Thr
1               5                   10                  15

Glu Leu Ser Ile Glu Ile Ala Ala Asn Gln Ser Trp Ala
            20                  25

<210> SEQ ID NO 19
<211> LENGTH: 30
<212> TYPE: PRT
<213> ORGANISM: Artificial Sequence
<220> FEATURE:
<223> OTHER INFORMATION: epislon-toxin beta hairpin region

<400> SEQUENCE: 19

Ser Ile Gln Ala Thr Ala Lys Phe Thr Val Pro Phe Asn Glu Thr Gly
1               5                   10                  15
```

```
Val Ser Leu Thr Thr Ser Tyr Ser Phe Ala Asn Thr Asn Thr
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Hemolytic beta hairpin region

<400> SEQUENCE: 20

Ala Val Gly Thr Ala Phe Lys Ala Gly Val Pro Ile Phe Ala Glu Thr
1               5                   10                  15

Glu Phe Lys Val Asp Ile Ser Val Asp Asn Gln Trp Asn Trp Gly
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Enterotoxin beta hairpin region

<400> SEQUENCE: 21

Glu Val Ser Ile Asn Val Asn Phe Ser Val Gly Phe Thr Ser Glu Phe
1               5                   10                  15

Ile Gln Ala Ser Val Glu Tyr Gly Phe Gly Ile Thr Ile Gly Glu Gln
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Alpha-hemolysin beta hairpin region

<400> SEQUENCE: 22

Thr Leu Thr Tyr Gly Phe Asn Gly Asn Val Thr Gly Asp Asp Thr Gly
1               5                   10                  15

Lys Ile Gly Gly Leu Ile Gly Ala Asn Val Ser Ile Gly His Thr
            20                  25                  30
```